United States Patent
Kiriyama et al.

(10) Patent No.: US 12,092,957 B2
(45) Date of Patent: Sep. 17, 2024

(54) RADIATION-SENSITIVE RESIN COMPOSITION, METHOD FOR FORMING RESIST PATTERN AND COMPOUND

(71) Applicant: JSR CORPORATION, Tokyo (JP)

(72) Inventors: Kazuya Kiriyama, Tokyo (JP); Katsuaki Nishikori, Tokyo (JP); Takuhiro Taniguchi, Tokyo (JP); Ryuichi Nemoto, Tokyo (JP); Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 369 days.

(21) Appl. No.: 17/508,191

(22) Filed: Oct. 22, 2021

(65) Prior Publication Data
US 2022/0043350 A1     Feb. 10, 2022

Related U.S. Application Data

(63) Continuation-in-part of application No. PCT/JP2020/019254, filed on May 14, 2020.

(30) Foreign Application Priority Data

May 27, 2019     (JP) .................................. 2019-098401

(51) Int. Cl.
| | |
|---|---|
| *G03F 7/039* | (2006.01) |
| *C07C 31/13* | (2006.01) |
| *C07C 69/608* | (2006.01) |
| *G03F 7/20* | (2006.01) |
| *G03F 7/32* | (2006.01) |

(52) U.S. Cl.
CPC ............ *G03F 7/0392* (2013.01); *C07C 31/13* (2013.01); *C07C 69/608* (2013.01); *G03F 7/2006* (2013.01); *G03F 7/327* (2013.01)

(58) Field of Classification Search
CPC .............................. C07C 69/608; G03F 7/0045
See application file for complete search history.

(56) References Cited

U.S. PATENT DOCUMENTS

| | | | | |
|---|---|---|---|---|
| 2013/0115556 A1* | 5/2013 | Iwato | .................... | G03F 7/0397 430/285.1 |
| 2016/0238930 A1* | 8/2016 | Fukushima | ........... | C08F 228/06 |
| 2016/0377979 A1* | 12/2016 | Miyagawa | ................ | G03F 7/38 430/270.1 |
| 2017/0008982 A1* | 1/2017 | Adachi | ................ | C07D 307/00 |

FOREIGN PATENT DOCUMENTS

| | | |
|---|---|---|
| JP | 2004029542 A | 1/2004 |
| JP | 4439270 B2 | 3/2010 |
| JP | 2012008500 A | 1/2012 |

OTHER PUBLICATIONS

International Search Report issued Jul. 28, 2020 in PCT/JP2020/019254, 4 pages.
William Adcock et al, "Synthesis of 4-Substituted Bicyclo [2.2.2]oct-1-yl Fluorides", J. Org. Chem., vol. 47, No. 15, 1982, pp. 2951-2957.
Translation of the International Preliminary Report on Patentability and Written Opinion issued Dec. 9, 2021 in PCT/JP2020/019254, 6 pages.
Office Action issued Jan. 30, 2024 in corresponding Japanese Patent Application No. 2021-522200 (with English translation), 5 pages.

\* cited by examiner

*Primary Examiner* — Mark F. Huff
*Assistant Examiner* — Nicholas E Brown
(74) *Attorney, Agent, or Firm* — Element IP, PLC

(57) ABSTRACT

A radiation-sensitive resin composition includes a resin having a partial structure represented by formula (1). $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded; $R^3$ represents a monovalent alicyclic hydrocarbon group having 4 to 20 carbon atoms and containing a fluorine atom. No fluorine atom is bonded to carbon atoms located at α-, β- and γ-positions of the carbon atom to which $R^1$ and $R^2$ are bonded; and No fluorine atom is bonded to carbon atoms located at α- and β-positions of the carbon atom to which $R^3$ is bonded.

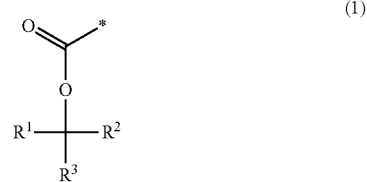

(1)

19 Claims, No Drawings

RADIATION-SENSITIVE RESIN COMPOSITION, METHOD FOR FORMING RESIST PATTERN AND COMPOUND

CROSS-REFERENCE TO RELATED APPLICATIONS

The present application is a continuation-in-part application of International Application No. PCT/JP2020/019254, filed May 14, 2020, which claims priority to Japanese Patent Application No. 2019-098401, filed May 27, 2019. The contents of these applications are incorporated herein by reference in their entirety.

BACKGROUND OF THE INVENTION

Field of the Invention

The present invention relates to a radiation-sensitive resin composition, a method for forming a resist pattern and a compound.

Description of the Related Art

A photolithography technology using a resist composition has been used for the fine circuit formation in a semiconductor device. As the representative procedure, for example, a resist pattern is formed on a substrate by generating an acid by irradiating the coating of the resist composition with a radioactive ray through a mask pattern, and then reacting in the presence of the acid as a catalyst to generate the difference of solubility of a resin into an alkaline or organic developer between an exposed part and a non-exposed part.

In the photolithography technology, the micronization of the pattern is promoted by using a short wave length radioactive ray such as ArF excimer laser, and by using immersion exposure method (liquid immersion lithography) in which the exposure is carried out in a liquid medium filled in the space between a lens of an exposing apparatus and a resist film. As a next generation technology, a lithography using a short wave length such as an electron beam, X ray and EUV (extreme ultraviolet ray) has been studied.

With progress of the exposing technology, a technology for achieving a pattern resolution from micron size to submicron size using a resist composition containing a resin having an alicyclic group has been developed (JP-B-4439270).

SUMMARY OF THE INVENTION

According to an aspect of the present invention, a radiation-sensitive resin composition includes: a resin having a partial structure represented by formula (1); a radiation-sensitive acid generator; and a solvent.

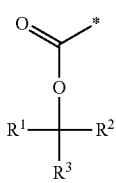

In the formula (1), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded; $R^3$ represents a monovalent alicyclic hydrocarbon group having 4 to 20 carbon atoms and containing a fluorine atom; provided that in $R^1$ and $R^2$, no fluorine atom is bonded to carbon atoms located at α-, β- and γ-positions of the carbon atom to which $R^1$ and $R^2$ are bonded; in $R^3$, no fluorine atom is bonded to carbon atoms located at α- and β-positions of the carbon atom to which $R^3$ is bonded; and * represents a bond.

According to another aspect of the present invention, a method for forming a resist pattern, includes: forming a resist film from the above-mentioned radiation-sensitive resin composition; exposing the resist film; and developing the exposed resist film.

According to a further aspect of the present invention, a compound is represented by formula (I).

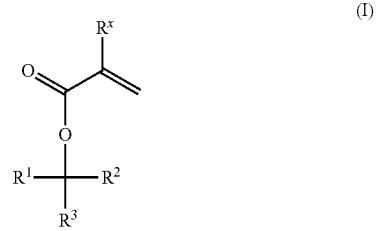

In the formula (I), $R^x$ is a hydrogen atom, a fluorine atom, a methyl group, or a trifluoromethyl group; $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded; $R^3$ represents a monovalent alicyclic hydrocarbon group having 4 to 20 carbon atoms and containing a fluorine atom; provided that in $R^1$ and $R^2$, no fluorine atom is bonded to carbon atoms located at α-, β- and γ-positions of the carbon atom to which $R^1$ and $R^2$ are bonded; and in $R^3$, no fluorine atom is bonded to carbon atoms located at α- and β-positions of the carbon atom to which $R^3$ is bonded.

According to a further aspect of the present invention, a compound is represented by formula (i).

In the formula (i), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded; $R^3$ represents a monovalent alicyclic hydrocarbon group having 4 to 20 carbon atoms and containing a fluorine atom; provided that in $R^1$ and $R^2$, no fluorine atom is bonded to carbon atoms located at α-, β- and γ-positions of the carbon atom to which $R^1$ and $R^2$ are bonded; and in $R^3$, no fluorine atom is bonded to carbon atoms located at α- and β-positions of the carbon atom to which $R^3$ is bonded.

DETAILED DESCRIPTION OF THE PREFERRED EMBODIMENTS

In recent years, with progress of micronization of resist patterns, critical dimension uniformity (CDU) performance that is an index of the uniformity of a line width and a hole diameter, line width roughness (LWR) performance that shows a variation of the line width of the resist pattern, and defect-suppression performance that suppresses watermark defects and residue defects are required, and various resist performances are required to be further improved. Furthermore, even in a next generation exposing technology such as electron beam exposure, various resist performances equivalent to or higher than those of an exposing technology using an ArF excimer laser are required.

The present invention relates, in one embodiment, to a radiation-sensitive resin composition containing:
a resin having a partial structure represented by the following formula (1);
a radiation-sensitive acid generator; and
a solvent,

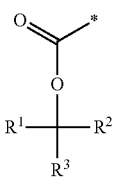
(1)

(in the formula (1),
$R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which the groups are bonded;
$R^3$ represents a monovalent alicyclic hydrocarbon group having 4 to 20 carbon atoms and containing a fluorine atom;
provided that in $R^1$ and $R^2$, no fluorine atom is bonded to carbon atoms located at α-, β- and γ-positions of the carbon atom to which $R^1$ and $R^2$ are bonded;
in $R^3$, no fluorine atom is bonded to carbon atoms located at α- and β-positions of the carbon atom to which $R^3$ is bonded; and
* represents a bond.)

The radiation-sensitive resin composition contains the resin having the partial structure represented by the above formula (1), whereby, even in exposure with not only an ArF excimer laser or the like but also EUV (extreme ultraviolet light) or the like, a resist film using the composition can exhibit CDU performance, LWR performance, and defect-suppression performance at a sufficient level. The reason for this is, without being bound by any theory, presumed to be that, for example, in the case of exposure with an ArF excimer laser, solubility contrast between an exposed part and a non-exposed part is improved by the fluorine atom introduced into the specific partial structure, thereby improving the rectangularity of a pattern. In the case of exposure with extreme ultraviolet light (EUV), it is presumed that the fluorine atom introduced into the specific partial structure improves an EUV absorption amount in the entire resin, and increases a secondary electron generation efficiency to increase an acid generation amount, thereby improving the solubility contrast to improve the rectangularity of the pattern. Furthermore, the introduction of fluorine atom into the resin provides improved water repellency of the resist film, whereby watermark defects can be suppressed. In addition, it is presumed that no fluorine atom is introduced into the vicinity of a deprotection site in the specific partial structure, whereby deprotection with a generated acid can be caused to smoothly proceed, and residue defects can also be suppressed while sensitivity is secured.

In one embodiment, the partial structure represented by the above formula (1) is preferably a partial structure represented by the following formula (1-1-1), a partial structure represented by the following formula (1-1-2), a partial structure represented by the following formula (1-1-3), or a partial structure represented by the following formula (1-1-4):

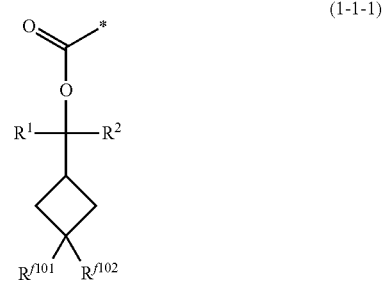
(1-1-1)

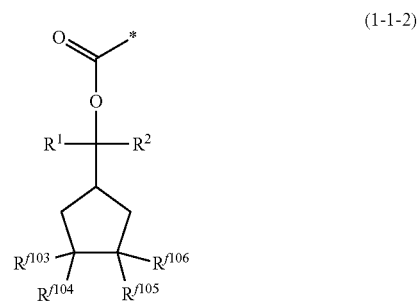
(1-1-2)

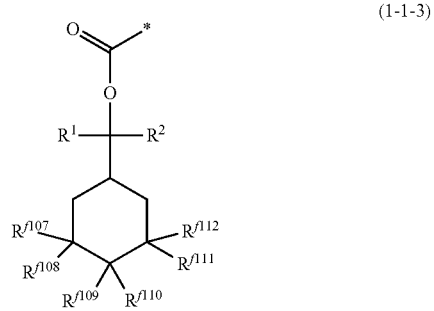
(1-1-3)

-continued (1-1-4)

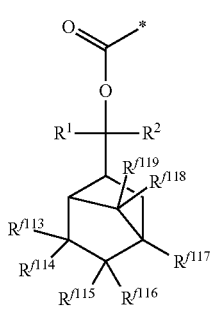

(in the formulae (1-1-1), (1-1-2), (1-1-3), and (1-1-4), $R^1$ and $R^2$ have the same meanings as those in the above formula (1);

$R'^{101}$ to $R'^{119}$ each independently represent a fluorine atom, a fluorinated alkyl group having 1 to 3 carbon atoms, a hydrogen atom, or an alkyl group having 1 to 3 carbon atoms; provided that at least one of $R'^{101}$ and $R'^{102}$, at least one of $R'^{103}$ to $R'^{106}$, at least one of $R'^{107}$ to $R'^{112}$, and at least one of $R'^{113}$ to $R'^{119}$ are fluorine atoms or fluorinated alkyl groups; and

* represents a bond.)

In another embodiment, the partial structure represented by the above formula (1) is preferably a partial structure represented by the following formula (1-2-1), a partial structure represented by the following formula (1-2-2), or a partial structure represented by the following formula (1-2-3);

(1-2-1)

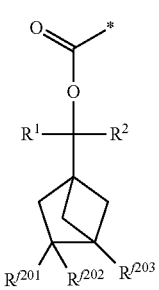

(1-2-2)

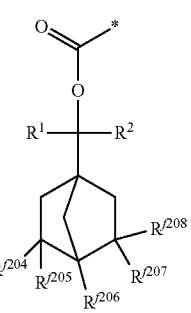

(1-2-3)

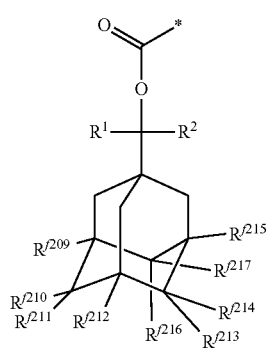

(in the formulae (1-2-1), (1-2-2), and (1-2-3), $R^1$ and $R^2$ have the same meanings as those in the above formula (1);

$R'^{201}$ to $R'^{217}$ each independently represent a fluorine atom, a fluorinated alkyl group having 1 to 3 carbon atoms, a hydrogen atom, or an alkyl group having 1 to 3 carbon atoms; provided that at least one of $R'^{201}$ to $R'^{203}$, at least one of $R'^{204}$ to $R'^{208}$, and at least one of $R'^{209}$ to $R'^{217}$ are fluorine atoms or fluorinated alkyl groups; and

* represents a bond.)

In one embodiment, by employing the partial structure represented by the above formula (1-1-1), the partial structure represented by the above formula (1-1-2), the partial structure represented by the above formula (1-1-3) or the partial structure represented by the above formula (1-1-4), or the partial structure represented by the above formula (1-2-1), the partial structure represented by the above formula (1-2-2), or the partial structure represented by the above formula (1-2-3) as the partial structure of the resin, CDU performance, LWR performance, and defect-suppression performance can be exhibited at a higher level.

In one embodiment, the fluorine atom is preferably directly bonded to the carbon atom constituting the alicyclic hydrocarbon group in $R^3$ of the above formula (1). In particular, the alicyclic hydrocarbon group preferably has a structure represented by $-CF_2-$. Thus, the deprotection due to the generated acid, of the deprotected site in the specific partial structure can be caused to more smoothly proceed.

In one embodiment, a content of a structural unit having the partial structure represented by the above formula (1) in the resin is preferably 5 mol % or more and 40 mol % or less. Thus, a resist film obtained with use of the radiation-sensitive resin composition can exhibit CDU performance, LWR performance, and defect-suppression performance at a higher level.

The present invention relates, in one embodiment, to a method for forming a resist pattern, including the steps of:
forming a resist film from the radiation-sensitive resin composition;
exposing the resist film; and
developing the exposed resist film.

In the forming method, the radiation-sensitive resin composition having excellent various resist performances is used, whereby a high-quality resist pattern can be efficiently formed.

In one embodiment, the exposure can be suitably performed with use of ArF excimer laser light or extreme ultraviolet light.

The present invention relates, in one embodiment, to a compound represented by the following formula (I):

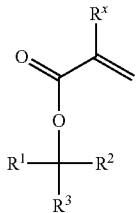

(in the formula (I),
$R^x$ is a hydrogen atom, a fluorine atom, a methyl group, or a trifluoromethyl group;
$R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which the groups are bonded;
$R^3$ represents a monovalent alicyclic hydrocarbon group having 4 to 20 carbon atoms and containing a fluorine atom;
provided that in $R^1$ and $R^2$, no fluorine atom is bonded to carbon atoms located at α-, β- and γ-positions of the carbon atom to which $R^1$ and $R^2$ are bonded; and
in $R^3$, no fluorine atom is bonded to carbon atoms located at α- and β-positions of the carbon atom to which $R^3$ is bonded.)

The compound has the specific structure represented by the above formula (I), whereby a highly functional material (resin or the like) can be suitably provided with use of the compound as a monomer.

The present invention relates, in one embodiment, to a compound represented by the following formula (i):

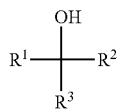

(in the formula (i),
$R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which the groups are bonded;
$R^3$ represents a monovalent alicyclic hydrocarbon group having 4 to 20 carbon atoms and containing a fluorine atom;
provided that in $R^1$ and $R^2$, no fluorine atom is bonded to carbon atoms located at α-, β- and γ-positions of the carbon atom to which $R^1$ and $R^2$ are bonded; and
in $R^3$, no fluorine atom is bonded to carbon atoms located at α- and β-positions of the carbon atom to which $R^3$ is bonded.)

The compound has the specific structure represented by the above formula (i), whereby a monomer for forming a highly functional material can be efficiently produced by causing an esterification reaction of the compound with, for example, a polymerizable group-containing carboxylic acid compound or a derivative thereof to proceed.

First Embodiment

<Radiation-Sensitive Resin Composition>

A radiation-sensitive resin composition according to the present embodiment (hereinafter, also simply referred to as a "composition") contains a resin, a radiation-sensitive acid generator, and a solvent. The composition may contain other optional components as long as the effects of the present invention are not impaired.

[Resin]

The resin is an aggregate of polymers, each polymer having a partial structure (hereinafter, also referred to as a "specific partial structure") represented by the following formula (1) (hereinafter, the resin is also referred to as a "base resin").

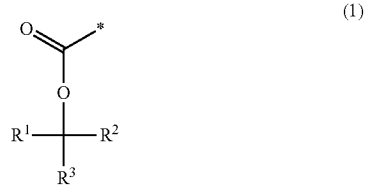

In the above formula (1), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with a carbon atom to which the groups are bonded.

$R^3$ represents a monovalent alicyclic hydrocarbon group having 4 to 20 carbon atoms and containing a fluorine atom.

Provided that in $R^1$ and $R^2$, no fluorine atom is bonded to carbon atoms located at α-, β- and γ-positions of the carbon atom to which $R^1$ and $R^2$ are bonded.

In $R^3$, no fluorine atom is bonded to carbon atoms located at α- and β-positions of a carbon atom to which $R^3$ is bonded.

* represents a bond.

The radiation-sensitive resin composition has excellent CDU performance, LWR performance, and defect-suppression performance because the resin has the specific partial structure.

In the above formula (1), the substituted or unsubstituted chain aliphatic hydrocarbon group having 1 to 6 carbon atoms, represented by $R^1$ and $R^2$ may be saturated or unsaturated. Examples of such a chain aliphatic hydrocarbon group include:
  alkyl groups such as a methyl group, an ethyl group, a n-propyl group, an i-propyl group, a n-butyl group, a 2-methylpropyl group, a 1-methylpropyl group, and a t-butyl group;
  alkenyl groups such as an ethenyl group, a propenyl group, and a butenyl group;
  alkynyl groups such as an ethynyl group, a propynyl group, and a butynyl group; and
  groups in which a hydrogen atom contained therein is substituted.

The substituted or unsubstituted alicyclic hydrocarbon group having 3 to 6 carbon atoms, represented by $R^1$ and $R^2$ may be saturated or unsaturated. Examples of such an alicyclic hydrocarbon group include:

monocyclic cycloalkyl groups such as a cyclopropyl group, a cyclobutyl group, a cyclopentyl group, and a cyclohexyl group;

cycloalkenyl groups such as a cyclopropenyl group, a cyclobutenyl group, a cyclopentenyl group, and a cyclohexenyl group;

polycyclic cycloalkyl groups such as a bicyclo[1.1.0] butyl group, a bicyclo[1.1.1]pentyl group, a bicyclo[2.1.1]hexyl group, a bicyclo[2.2.0]hexyl group, and a bicyclo[3.1.0]hexyl group; and groups in which a hydrogen atom contained therein is substituted.

The 3- to 6-membered cyclic structure that is formed by bonding $R^1$ and $R^2$ to each other with a carbon atom to which $R^1$ and $R^2$ are bonded is not particularly limited as long as it is a carbocyclic ring of the substituted or unsubstituted alicyclic hydrocarbon group having 3 to 6 carbon atoms. The carbocyclic ring of such an alicyclic hydrocarbon group may be saturated or unsaturated. Among them, monocyclic saturated alicyclic hydrocarbon rings such as a cyclopentane ring and a cyclohexane ring, and monocyclic unsaturated alicyclic hydrocarbon rings such as a cyclopentene ring and a cyclohexene ring are preferable.

Examples of a substituent that may substitute the hydrogen atom of the chain aliphatic hydrocarbon group, the alicyclic hydrocarbon group, and the cyclic structure represented by $R^1$ and $R^2$ include: halogen atoms such as a fluorine atom, a chlorine atom, a bromine atom, and an iodine atom; a hydroxy group; a carboxy group; a cyano group; a nitro group; a linear or branched alkyl group having 1 to 8 carbon atoms; monocyclic or polycyclic cycloalkyl groups having 3 to carbon atoms; aryl groups such as a phenyl group, a 1-naphthyl group, and a 1-anthracenyl group; alkoxy groups such as a methoxy group, an ethoxy group, and a tert-butoxy group; alkoxycarbonyl groups such as a methoxycarbonyl group, a butoxycarbonyl group, and an adamantylmethyloxycarbonyl group; alkoxycarbonyloxy groups such as a methoxycarbonyloxy group, a butoxycarbonyloxy group, and an adamantylmethyloxycarbonyloxy group; acyl groups such as an acetyl group, a propionyl group, a benzoyl group, and an acryloyl group; and acyloxy groups such as an acetyloxy group, a propionyloxy group, a benzoyloxy group, and an acryloyloxy group.

Provided that in $R^1$ and $R^2$, no fluorine atom is bonded to carbon atoms located at $\alpha$-, $\beta$- and $\gamma$-positions of the carbon atom to which $R^1$ and $R^2$ are bonded; As described above, no fluorine atom is introduced into the vicinity of a deprotection site in the specific partial structure, whereby deprotection due to a generated acid can be caused to smoothly proceed, and residue defects can also be suppressed while the sensitivity is secured. A fluorine atom may be bonded to a carbon atom located at more distal position (at a position after the $\delta$ position) to the carbon atom located at the $\gamma$-position of the carbon atom to which $R^1$ and $R^2$ are bonded since the influence of the fluorine atom on deprotection ability in the specific partial structure is small.

When a fluorine atom is bonded to a carbon atom located after the $\gamma$-position of the carbon atom to which $R^1$ and $R^2$ are bonded, examples of $R^1$ and $R^2$ include a 4,4,4-trifluorobutyl group, a 5,5,5-trifluoropentyl group, and a 4,4,5,5,5-pentafluoropentyl group.

The monovalent alicyclic hydrocarbon group having 4 to carbon atoms and containing a fluorine atom, represented by $R^3$ is a group in which at least one of hydrogen atoms of the monovalent alicyclic hydrocarbon group having 4 to 20 carbon atoms is substituted with a fluorine atom. The remaining hydrogen atoms may be substituted with fluorine atoms, substituted with other substituents, or unsubstituted. Provided that in $R^3$, no fluorine atom is bonded to carbon atoms located at $\alpha$- and $\beta$-positions of a carbon atom to which $R^3$ is bonded in the above formula (1). As in the case of $R^1$ and $R^2$, no fluorine atom is introduced into the vicinity of the deprotection site in the specific partial structure, whereby the deprotection due to the generated acid can be caused to smoothly proceed, and the residue defects can also be suppressed while the sensitivity is secured. A fluorine atom may be bonded to a carbon atom located at more distal position (at a position after the $\gamma$-position) to the carbon atom located at the $\beta$-position of the carbon atom to which $R^3$ is bonded since the influence of the fluorine atom on the deprotection ability in the specific partial structure is small.

Examples of the monovalent alicyclic hydrocarbon group having 4 to 20 carbon atoms include a monocyclic or polycyclic saturated hydrocarbon group, or a monocyclic or polycyclic unsaturated hydrocarbon group. The monocyclic saturated hydrocarbon group is preferably a cyclopentyl group, a cyclohexyl group, a cycloheptyl group, or a cyclooctyl group. The polycyclic cycloalkyl group is preferably a bridged alicyclic hydrocarbon group such as a norbornyl group, an adamantyl group, a tricyclodecyl group, or a tetracyclododecyl group. The bridged alicyclic hydrocarbon group refers to a polycyclic alicyclic hydrocarbon group in which two carbon atoms which are not adjacent to each other among carbon atoms constituting an alicyclic ring are bonded by a bond chain containing one or more carbon atoms.

In $R^3$, as a substituent that substitutes some or all of hydrogen atoms other than hydrogen atoms on the carbon atoms located at the $\alpha$- and $\beta$-positions of the carbon atom to which $R^3$ is bonded, a substituent that substitutes hydrogen atoms in $R^1$ and $R^2$ can be suitably employed.

The partial structure represented by the above formula (1) is preferably a partial structure represented by the following formula (1-1-1), a partial structure represented by the following formula (1-1-2), a partial structure represented by the following formula (1-1-3), or a partial structure represented by the following formula (1-1-4).

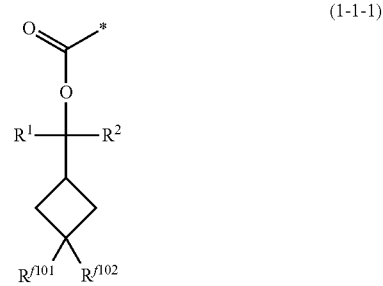

(1-1-1)

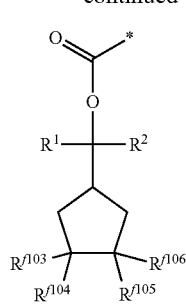
(1-1-2)

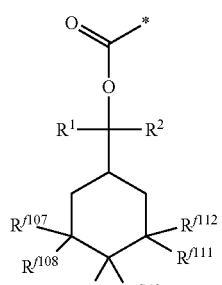
(1-1-3)

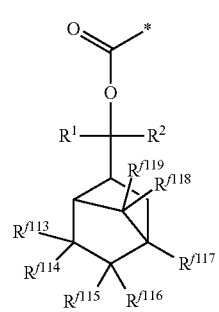
(1-1-4)

In the above formulae (1-1-1), (1-1-2), (1-1-3), and (1-1-4), $R^1$ and $R^2$ have the same meanings as those in the above formula (1).

$R^{f101}$ to $R^{f119}$ each independently represent a fluorine atom, a fluorinated alkyl group having 1 to 3 carbon atoms, a hydrogen atom, or an alkyl group having 1 to 3 carbon atoms. Provided that at least one of $R^{f101}$ and $R^{f102}$, at least one of $R^{f103}$ to $R^{f106}$, at least one of $R^{f107}$ to $R^{f112}$, and at least one of $R^{f113}$ to $R^{f119}$ are a fluorine atom or a fluorinated alkyl group.

Examples of the alkyl group having 1 to 3 carbon atoms, represented by $R^{f101}$ to $R^{f119}$ include a methyl group, an ethyl group, a propyl group, and an i-propyl group, and examples of the fluorinated alkyl group having 1 to 3 carbon atoms include groups in which some or all of hydrogen atoms of these alkyl groups are substituted with fluorine atoms. Specific examples thereof include a trifluoromethyl group, a 2,2,2-trifluoroethyl group, and a 1,1,1,3,3,3-hexafluoro-2-propyl group.

In the formula (1-1-1), at least one of $R^{f101}$ and $R^{f102}$ is preferably a fluorine atom. Among them, $R^{f101}$ and $R^{f102}$ are more preferably a fluorine atom. In the formula (1-1-2), at least one of $R^{f103}$ to $R^{f106}$ is preferably a fluorine atom. Among them, it is more preferable that $R^{f103}$ and $R^{f104}$ are a fluorine atom; $R^{f105}$ and $R^{f106}$ are a fluorine atom, or a combination thereof is used. In the formula (1-1-3), at least one of $R^{f107}$ to $R^{f112}$ is preferably a fluorine atom. Among them, it is preferable that $R^{f107}$ and $R^{f108}$ are a fluorine atom; $R^{f109}$ and $R^{f110}$ are a fluorine atom; $R^{f111}$ and $R^{f112}$ are a fluorine atom; or a combination thereof is used. In the formula (1-1-4), at least one of $R^{f113}$ to $R^{f119}$ is preferably a fluorine atom. Among them, it is more preferable that $R^{f113}$ and $R^{f114}$ are a fluorine atom; $R^{f115}$ and $R^{f116}$ are a fluorine atom; $R^{f118}$ and $R^{f119}$ are a fluorine atom; or a combination thereof is used.

The base resin may have each of the partial structure represented by the above formula (1-1-1), the partial structure represented by the above formula (1-1-2), the partial structure represented by the above formula (1-1-3), and the partial structure represented by the above formula (1-1-4) alone, or may have a plurality of them in combination.

The partial structure represented by the above formula (1) is preferably a partial structure represented by the following formula (1-2-1), a partial structure represented by the following formula (1-2-2), or a partial structure represented by the following formula (1-2-3), in place of or in addition to the partial structures represented by the above formulae (1-1-1) to (1-1-4).

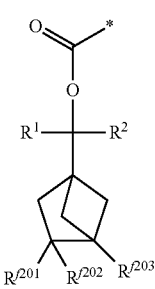
(1-2-1)

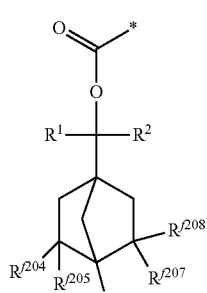
(1-2-2)

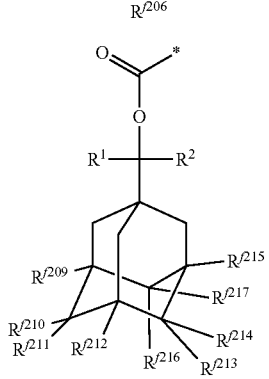
(1-2-3)

In the above formulae (1-2-1), (1-2-2), and (1-2-3), $R^1$ and $R^2$ have the same meanings as those in the above formula (1).

$R^{f201}$ to $R^{f217}$ each independently represent a fluorine atom, a fluorinated alkyl group having 1 to 3 carbon atoms, a hydrogen atom, or an alkyl group having 1 to 3 carbon atoms. Provided that at least one of $R^{f201}$ to $R^{f203}$, at least one of $R^{204}$ to $R'^{208}$, and at least one of $R'^{209}$ to $R'^{217}$ are a fluorine atom or a fluorinated alkyl group.

* represents a bond.

As the alkyl group having 1 to 3 carbon atoms and the fluorinated alkyl group having 1 to 3 carbon atoms, represented by $R'^{201}$ to $R'^{217}$, the alkyl group having 1 to 3 carbon atoms and the fluorinated alkyl group having 1 to 3 carbon atoms, represented by $R'^{101}$ to $R'^{118}$ can be suitably employed.

In the formula (1-2-1), at least one of $R'^{201}$ to $R'^{203}$ is preferably a fluorine atom. Among them, $R'^{201}$ and $R'^{202}$ are more preferably fluorine atoms. In the formula (1-2-2), at least one of $R'^{204}$ to $R'^{208}$ is preferably a fluorine atom. Among them, it is more preferable that $R'^{204}$ and $R'^{205}$ are fluorine atoms; $R'^{207}$ and $R'^{208}$ are a fluorine atoms; or a combination thereof is used. In the formula (1-2-3), at least one of $R'^{209}$ to $R'^{217}$ is preferably a fluorine atom. Among them, it is more preferable that $R'^{210}$ and $R'^{211}$ are fluorine atoms; $R'^{213}$ and $R'^{214}$ are fluorine atoms; $R'^{216}$ and $R'^{217}$ are fluorine atoms; or a combination thereof is used.

[Structural Unit (A)]

The containing mode of the specific partial structure in the resin is not particularly limited, but the specific partial structure is suitably introduced as a side chain structure for the main chain of the polymer. The specific partial structure is preferably introduced as a side chain structure of a structural unit (hereinafter, also referred to as a "structural unit (A)") represented by the following formula (A) into the resin.

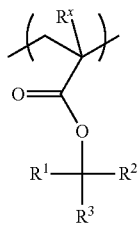

(A)

In the above formula (A), $R^x$ is a hydrogen atom, a methyl group, or a trifluoromethyl group.

$R^1$ to $R^3$ each have the same meanings as those in the above formula (1).

The structural unit (A) is preferably a structural unit represented by the following formula (A-1-1), a structural unit represented by the following formula (A-1-2), a structural unit represented by the following formula (A-1-3), or a structural unit represented by the following formula (A-1-4).

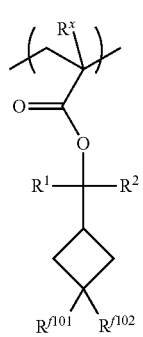

(A-1-1)

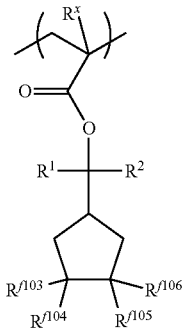

(A-1-2)

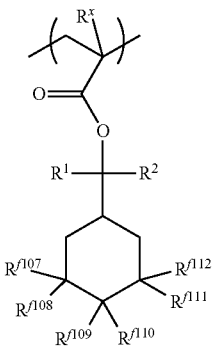

(A-1-3)

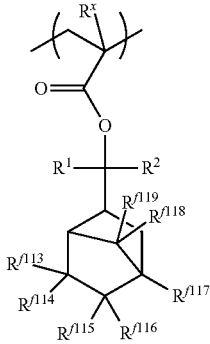

(A-1-4)

In the above formulae (A-1-1), (A-1-2), (A-1-3), and (A-1-4), $R^x$ has the same meaning as that in the above formula (A).

$R^1$ and $R^2$ have the same meanings as those in the above formula (1).

$R'^{101}$ to $R'^{119}$ have the same meanings as those in the above formulae (1-1-1), (1-1-2), (1-1-3), and (1-1-4).

The structural unit (A) is more preferably a structural unit represented by the above formula (A-1-1), a structural unit represented by the above formula (A-1-2), or a structural unit represented by the above formula (A-1-3), still more preferably a structural unit represented by the above formula (A-1-2) or a structural unit represented by the above formula (A-1-3), and particularly preferably a structural unit represented by the above formula (A-1-3).

The structural unit (A) is preferably a structural unit represented by the following formula (A-2-1), a structural unit represented by the following formula (A-2-2), or a structural unit represented by the following formula (A-2-3), in place of or in addition to the structural units represented by the above formulae (A-1-1) to (A-1-4).

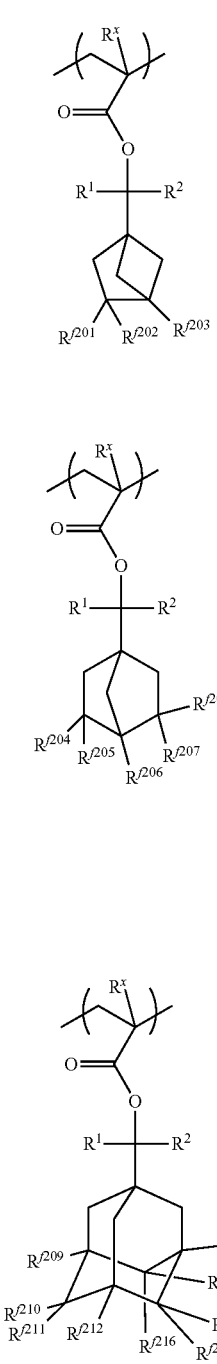

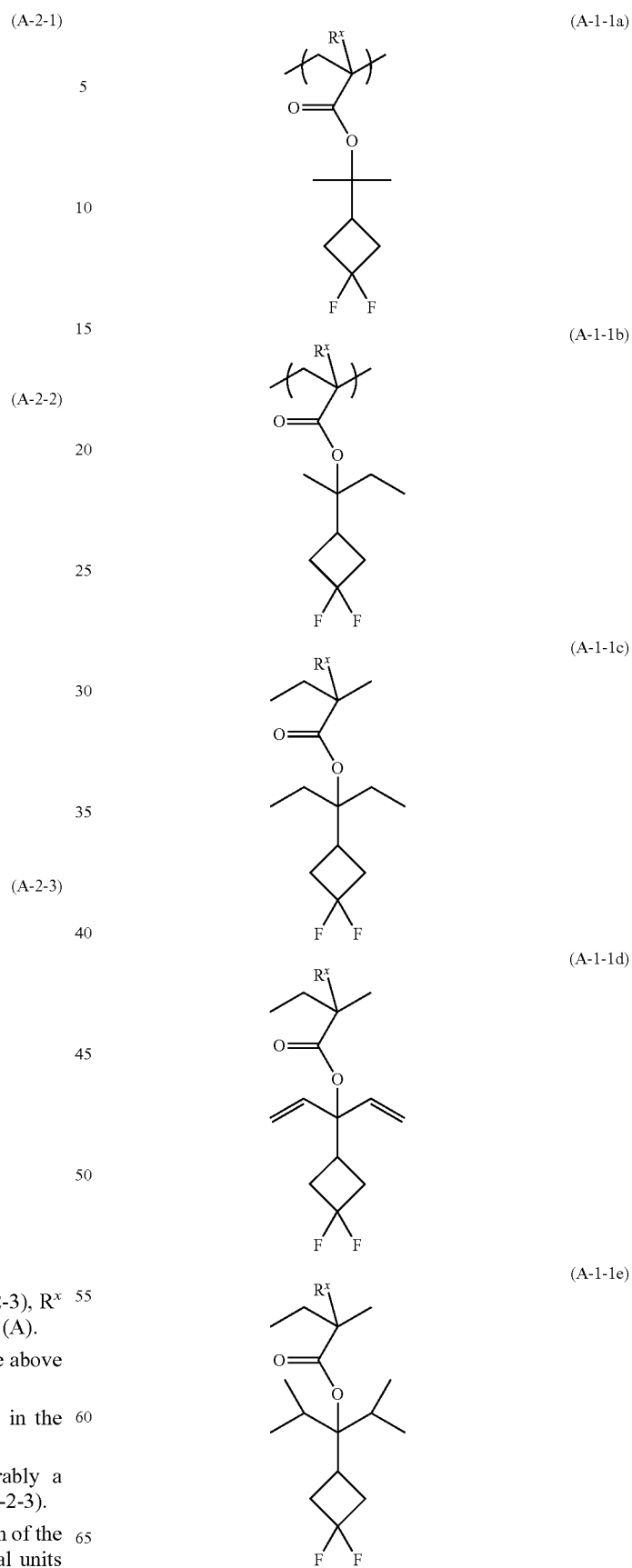

In the above formulae (A-2-1), (A-2-2), and (A-2-3), $R^x$ has the same meaning as that in the above formula (A).

$R^1$ and $R^2$ have the same meanings as those in the above formula (1).

$R'^{201}$ to $R'^{217}$ have the same meanings as those in the above formulae (1-2-1), (1-2-2), and (1-2-3).

Among them, the structural unit (A) is preferably a structural unit represented by the above formula (A-2-3).

Examples of the structural unit represented by each of the above formulae (A-1-1) to (A-1-4) include structural units represented by the following formulae.

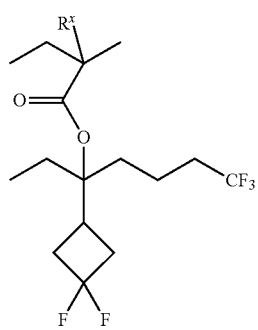 (A-1-1f)
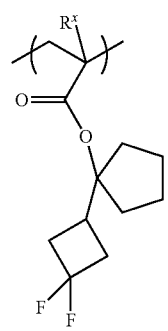 (A-1-1g)
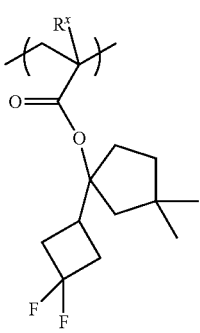 (A-1-1h)
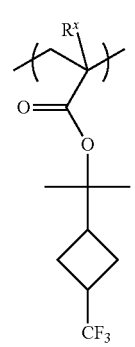 (A-1-1i)
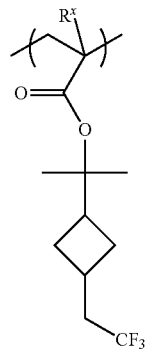 (A-1-1j)
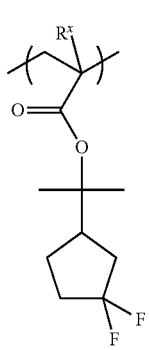 (A-1-2a)
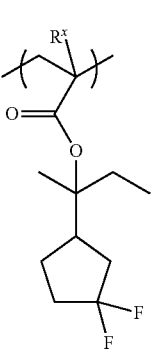 (A-1-2b)
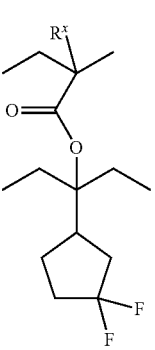 (A-1-2c)

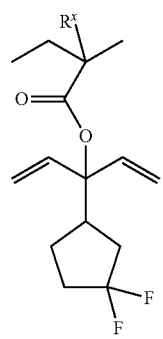 (A-1-2d)
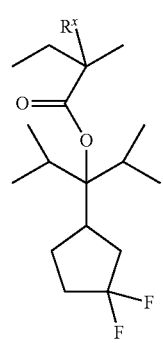 (A-1-2e)
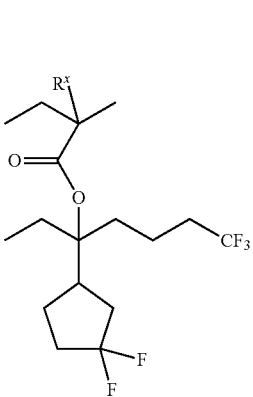 (A-1-2f)
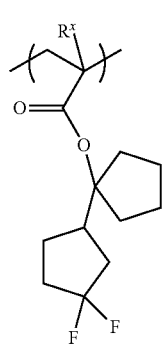 (A-1-2g)
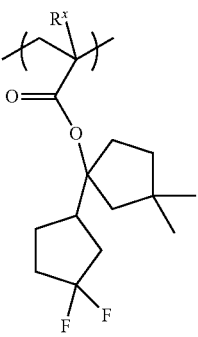 (A-1-2h)
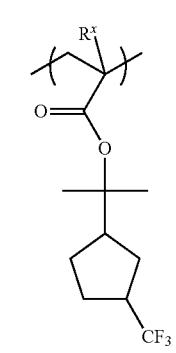 (A-1-2i)
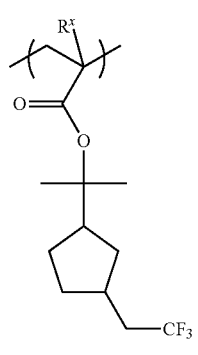 (A-1-2j)
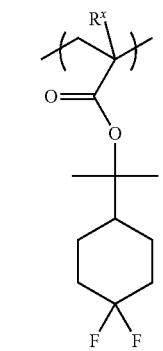 (A-1-3a)

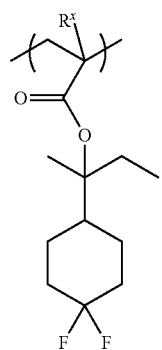 (A-1-3b)
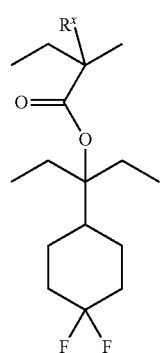 (A-1-3c)
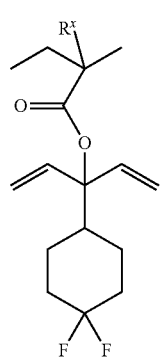 (A-1-3d)
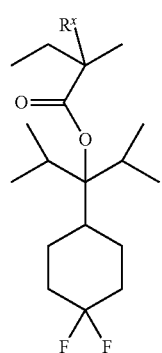 (A-1-3e)
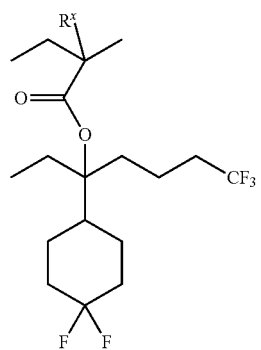 (A-1-3f)
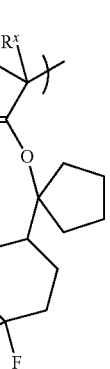 (A-1-3g)
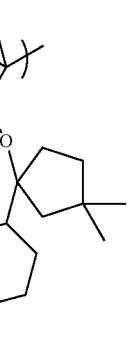 (A-1-3h)
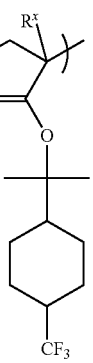 (A-1-3i)

-continued
(A-1-3j)
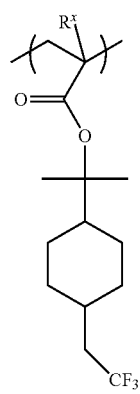
(A-1-3k)
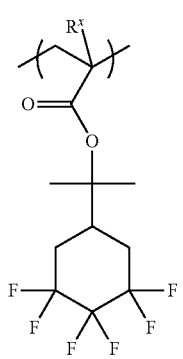
(A-1-3l)
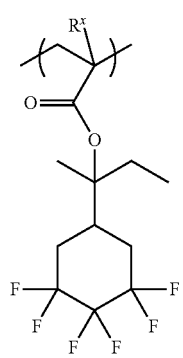
(A-1-3m)
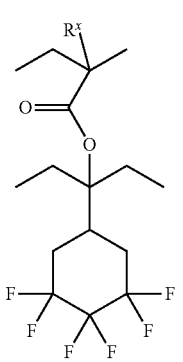
-continued
(A-1-3n)
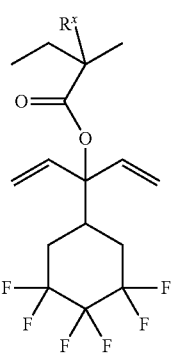
(A-1-3o)
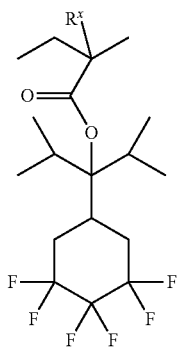
(A-1-3p)
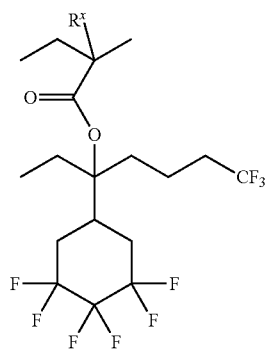
(A-1-3q)
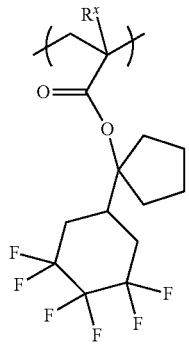

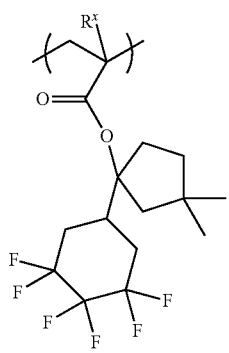 (A-1-3r)
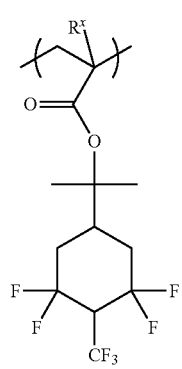 (A-1-3s)
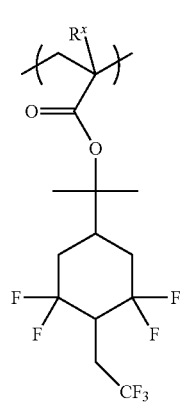 (A-1-3t)
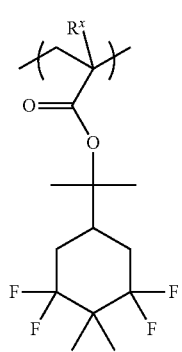 (A-1-3u)
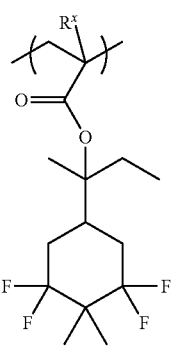 (A-1-3v)
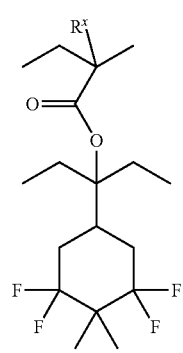 (A-1-3w)
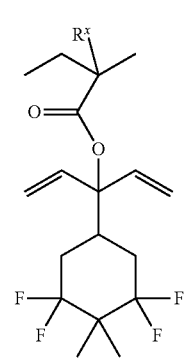 (A-1-3x)
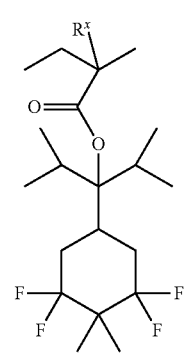 (A-1-3y)

(A-1-3z) 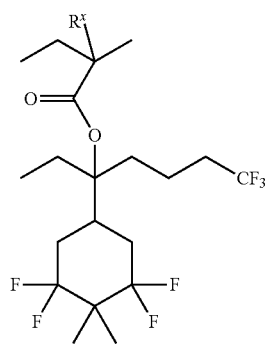
(A-1-3α) 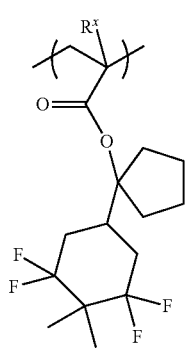
(A-1-3β) 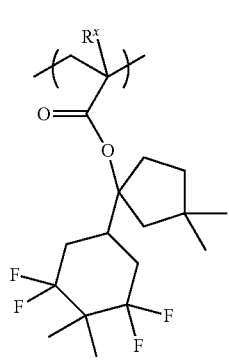
(A-1-4a) 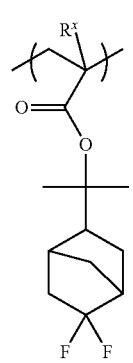
(A-1-4b) 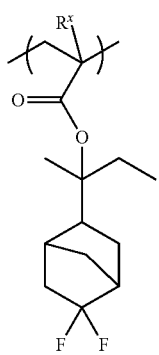
(A-1-4c) 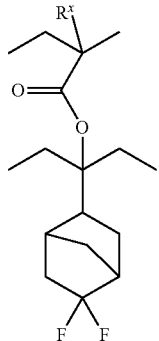
(A-1-4d) 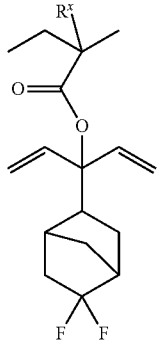
(A-1-4e) 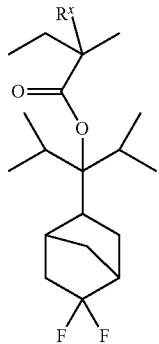

(A-1-4f) 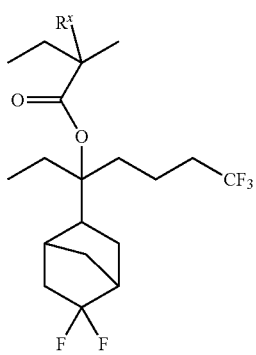
(A-1-4g) 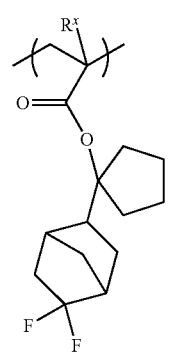
(A-1-4h) 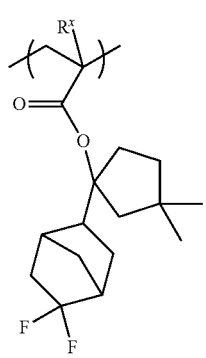
(A-1-4i) 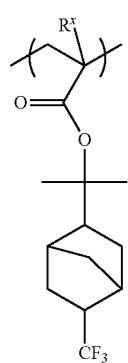
(A-1-4j) 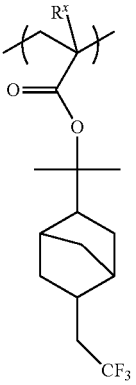
In the above formulae (A-1-1a) to (A-1-1j), (A-1-2a) to (A-1-2j), (A-1-3a) to (A-1-3z), (A-1-3α) to (A-1-3β), and (A-1-4a) to (A-1-4j), $R^x$ has the same meaning as that in the above formula (A).
Examples of the structural unit represented by each of the above formulae (A-2-1) to (A-2-3) include structural units represented by the following formulae.
(A-2-1a) 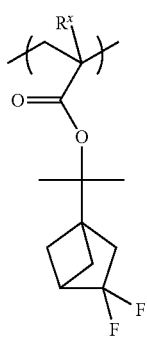
(A-2-1b) 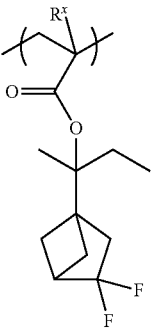
(A-2-1c) 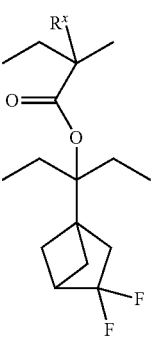

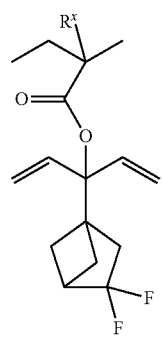 (A-2-1d)
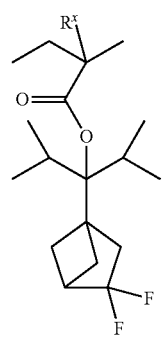 (A-2-1e)
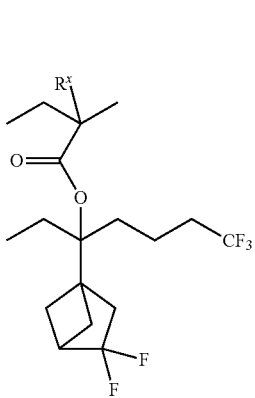 (A-2-1f)
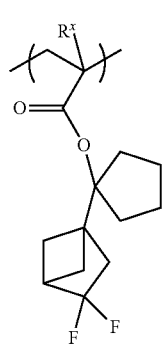 (A-2-1g)
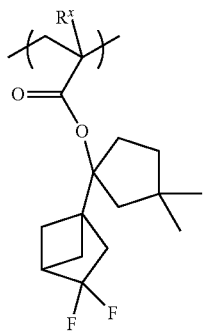 (A-2-1h)
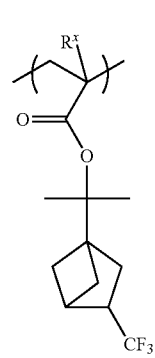 (A-2-1i)
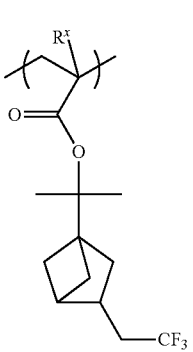 (A-2-1j)
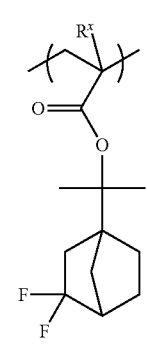 (A-2-2a)

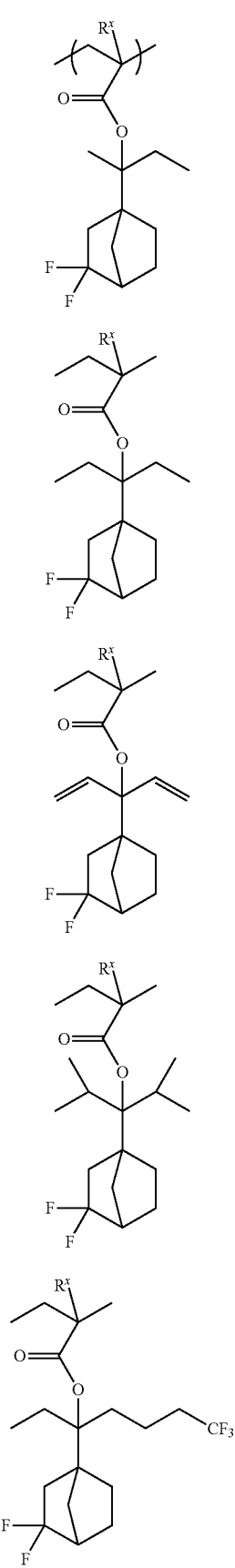
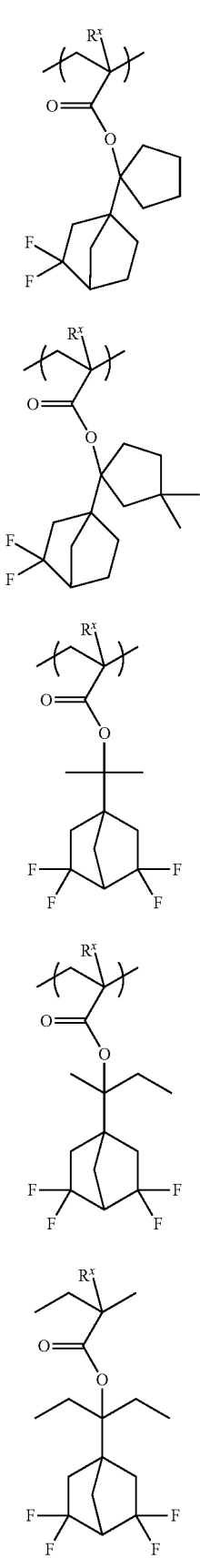

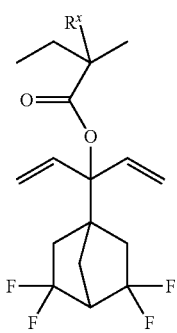
(A-2-2l)
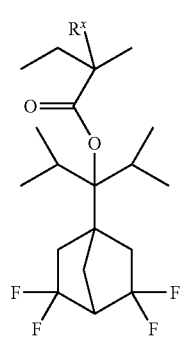
(A-2-2m)
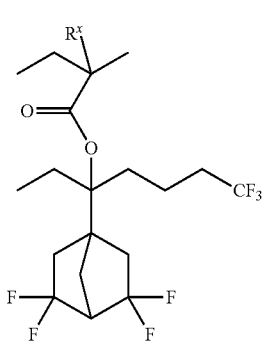
(A-2-2n)
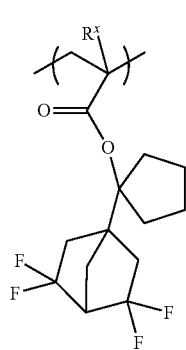
(A-2-2o)
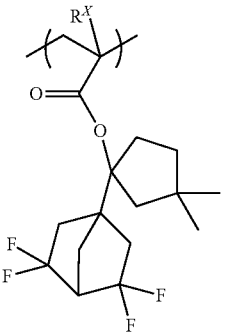
(A-2-2p)
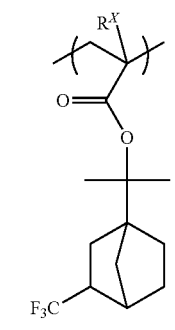
(A-2-2q)
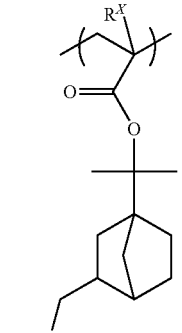
(A-2-2r)
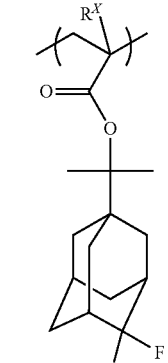
(A-2-3a)

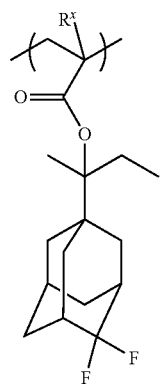 (A-2-3b)
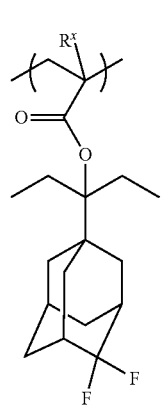 (A-2-3c)
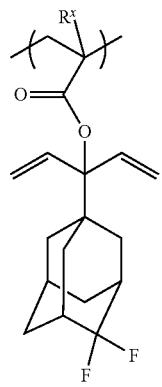 (A-2-3d)
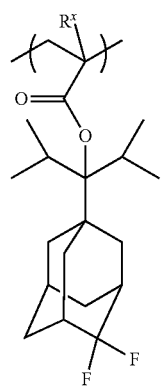 (A-2-3e)
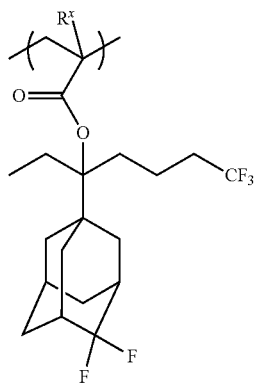 (A-2-3f)
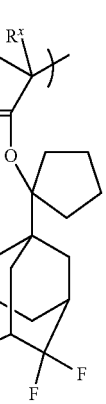 (A-2-3g)
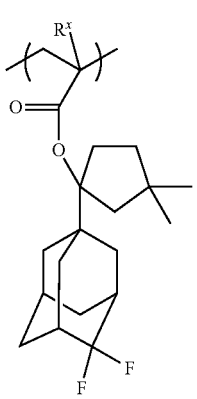 (A-2-3h)
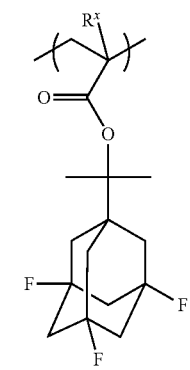 (A-2-i)

(A-2-3j)
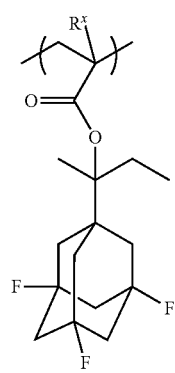
(A-2-3k)
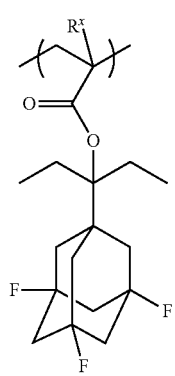
(A-2-3l)
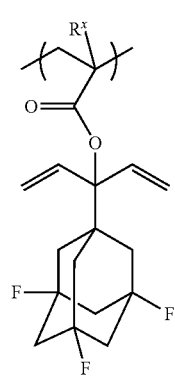
(A-2-3m)
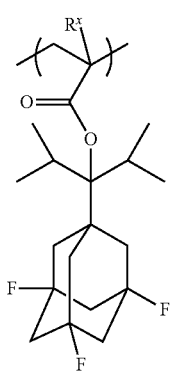
(A-2-3n)
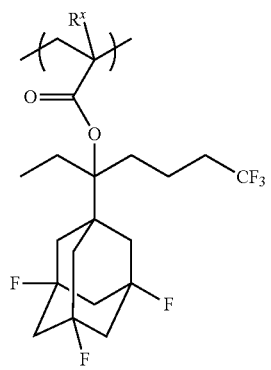
(A-2-3o)
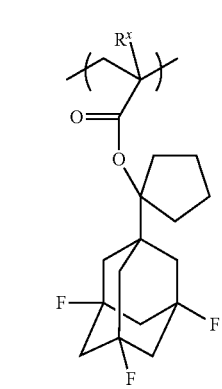
(A-2-3p)
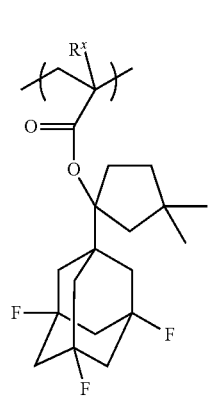
(A-2-3q)
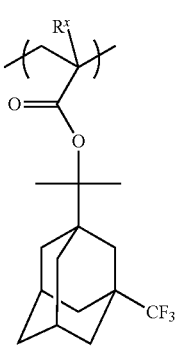

-continued

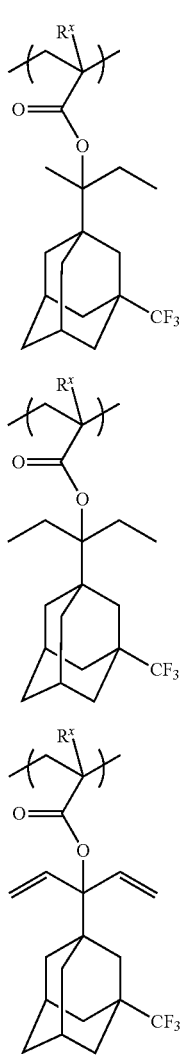

(A-2-3r)

(A-2-3s)

(A-2-3t)

In the above formulae (A-2-1a) to (A-2-1j), (A-2-2a) to (A-2-2r), and (A-2-3a) to (A-2-3t), $R^x$ has the same meaning as that in the above formula (A).

The base resin may contain one or a combination of two or more of the structural units (A).

The lower limit of the content ratio of the structural unit (A) is preferably 1 mol %, more preferably 2 mol %, still more preferably 3 mol %, and particularly preferably 5 mol %, with respect to the total structural units constituting the base resin. The upper limit of the content ratio is preferably 70 mol %, more preferably 60 mol %, still more preferably 50 mol %, and particularly preferably 40 mol %. By setting the content ratio of the structural unit (A) within the above range, the CDU performance, LWR performance, and defect-suppression performance of the resist film obtained from the radiation-sensitive resin composition can be further improved.

In addition to the structural unit (A), the base resin preferably has a structural unit containing an acid-dissociable group (hereinafter, also referred to as a "structural unit (B)"), and a structural unit (C) containing at least one selected from the group consisting of a lactone structure, a cyclic carbonate structure, and a sultone structure to be described later, and may have other structural units other than the structural units (B) and (C). The "acid-dissociable group" refers to a group that substitutes a hydrogen atom of a carboxy group, a phenolic hydroxyl group, an alcoholic hydroxyl group, or a sulfo group or the like, and is dissociated by the action of an acid. The radiation-sensitive resin composition has excellent patternability because the resin has the structural unit (B). Each structural unit will be described below.

[Structural Unit (B)]

The structural unit (B) is a structural unit having an acid-dissociable group. The structural unit (B) is not particularly limited as long as the unit has an acid-dissociable group. Examples of the structural unit (B) include a structural unit having a tertiary alkyl ester moiety; a structural unit having a structure in which a hydrogen atom in a phenolic hydroxide group is substituted with a tertiary alkyl group; and a structural unit having an acetal bond. In terms of improving the patternability of the radiation-sensitive resin composition, the structural unit (B) is preferably a structural unit represented by the following formula (2) (hereinafter, also referred to a "structural unit (B-1)").

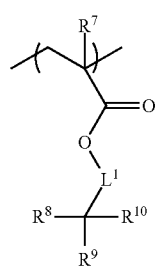

(2)

In the above formula (2), $R^7$ is a hydrogen atom, a fluorine atom, a methyl group, or a trifluoromethyl group; $R^8$ is a hydrogen atom, or a monovalent hydrocarbon group having a carbon number of 1 to 20; $R^9$ and $R^{10}$ are each independently a monovalent chain hydrocarbon group having a carbon number of 1 to 10, or a monovalent alicyclic hydrocarbon group having a carbon number of 3 to 20, or represent a divalent alicyclic group having a carbon number of 3 to 20, which is obtained by combining $R^9$ and $R^{10}$ with the carbon atom to which they are bound; $L^1$ represents a single bond, or a divalent linking group. However, when $L^1$ is the divalent linking group, a carbon atom which is bound to an oxygen atom of —COO— in the above formula (2) is a tertiary carbon, or its structure at the terminal side of the side chain is —COO—.

As $R^7$ described above, in terms of the copolymerizability of monomers resulting in the structural unit (B-1), a hydrogen atom or a methyl group is preferred. A methyl group is more preferred.

Examples of the monovalent hydrocarbon group having a carbon number of 1 to 20 represented by $R^8$ as described above include a chain hydrocarbon group having a carbon number of 1 to 10, a monovalent alicyclic hydrocarbon group having a carbon number of 3 to 20, and a monovalent aromatic hydrocarbon group having a carbon number of 6 to 20.

Examples of the chain hydrocarbon group having a carbon number of 1 to 10 represented by $R^8$ to $R^{10}$ as described above include a straight or branched chain saturated hydrocarbon group having a carbon number of 1 to 10, or a straight or branched chain unsaturated hydrocarbon group having a carbon number of 1 to 10.

Examples of the alicyclic a hydrocarbon group having a carbon number of 3 to 20 represented by $R^8$ to $R^{10}$ as described above include a monocyclic or polycyclic saturated hydrocarbon group, or a monocyclic or polycyclic unsaturated hydrocarbon group. Preferred examples of the monocyclic saturated hydrocarbon group include a cyclopentyl group, a cyclohexyl group, a cycloheptyl group, and a cyclooctyl group. Preferred examples of the polycyclic cycloalkyl group include a bridged alicyclic hydrocarbon group including a norbornyl group, an adamantyl group, a tricyclodecyl group, and a tetracyclododecyl group. The bridged alicyclic hydrocarbon group refers to a polycyclic alicyclic hydrocarbon group in which non-adjacent two carbon atoms of the alicyclic ring are bonded together via a binding chain having one or more carbon atoms.

Examples of the monovalent aromatic hydrocarbon group having a carbon number of 6 to 20 represented by $R^8$ as described above include an aryl group including a phenyl group, a tolyl group, a xylyl group, a naphthyl group, and an anthryl group; and an aralkyl group including a benzyl group, a phenethyl group, and a naphthyl methyl group.

Preferred examples of $R^8$ include a straight or branched chain saturated hydrocarbon group having a carbon number of 1 to 10, and an alicyclic hydrocarbon group having a carbon number of 3 to 20.

The divalent alicyclic group having a carbon number of 3 to 20, which is obtained by combining a combination of the chain hydrocarbon group or the alicyclic hydrocarbon group represented by $R^9$ and $R^{10}$ with the carbon atom to which they are bound, is not particularly limited as long as the group is a group obtained by removing two hydrogen atoms from the same carbon atom of a monocyclic or polycyclic alicyclic hydrocarbon carbocyclic ring having the same number of carbon atoms as described above. The group may be a monocyclic hydrocarbon group or a polycyclic hydrocarbon group. The polycyclic hydrocarbon group may be a bridged alicyclic hydrocarbon group or a fused alicyclic hydrocarbon group, and may be a saturated hydrocarbon group or an unsaturated hydrocarbon group. The fused alicyclic hydrocarbon group refers to a polycyclic alicyclic hydrocarbon group in which a plurality of alicyclic rings shares one side (a bond between adjacent two carbon atoms).

Preferred examples of the saturated hydrocarbon group in the monocyclic alicyclic hydrocarbon group include a cyclopentanediyl group, a cyclohexanediyl group, a cycloheptanediyl group, and a cyclooctanediyl group. Preferred examples of the unsaturated hydrocarbon group include a cyclopentenediyl group, a cyclohexenediyl group, a cycloheptenediyl group, a cyclooctenediyl group, and a cyclodecenediyl group. Preferred examples of the polycyclic alicyclic hydrocarbon group include a bridged alicyclic saturated hydrocarbon group. For example, a group such as a bicyclo[2.2.1]heptan-2,2-diyl group (a norbornane-2,2-diyl group), a bicyclo[2.2.2]octan-2,2-diyl group, or a tricyclo[3.3.1.1$^{3,7}$]decan-2,2-diyl group (an adamantane-2,2-diyl group) is preferred.

Examples of the divalent linking group represented by $L^1$ as described above include an alkanediyl group, a cycloalkanediyl group, an alkenediyl group, *—$R^{LA}$O—, and *—$R^{LB}$COO—. (* refers to a bond to the side of oxygen.) However, when the group is other than *—$R^{LB}$COO—, the carbon atom connecting to the oxygen atom of —COO— in the above formula (2) is a tertiary carbon, and the carbon atom does not have any hydrogen atom. The tertiary carbon is obtained when there are two bonds from the same carbon atom in the group, or when one or two substituent groups are further connected to the carbon atom having one of the bonds in the group. A part of or all of hydrogen atoms in the group may be substituted with a halogen atom including a fluorine atom or chlorine atom, or a cyano group.

The alkanediyl group is preferably an alkanediyl group having a carbon number of 1 to 8.

Examples of the cycloalkanediyl group include a monocyclic cycloalkanediyl group including a cyclopentanediyl group and a cyclohexanediyl group; and a polycyclic cycloalkanediyl group including a norbornanediyl group and an adamantanediyl group. The cycloalkanediyl group is preferably a cycloalkanediyl group having a carbon number of 5 to 12.

Examples of the alkenediyl group include an ethenediyl group, a propenediyl group, and a butenediyl group. The alkenediyl group is preferably an alkenediyl group having a carbon number of 2 to 6.

Examples of $R^{LA}$ in the *—$R^{LA}$O— include the alkanediyl group, the cycloalkanediyl group, and the alkenediyl group as each described above. Examples of $R^{LB}$ in *—$R^{LB}$COO— include the alkanediyl group, the cycloalkanediyl group, and the alkenediyl group as each described above, and an arenediyl group. Examples of the arenediyl group include a phenylene group, a tolylene group, and a naphthylene group. The arenediyl group is preferably an arenediyl group having a carbon number of 6 to 15.

Among them, preferably, $R^8$ is an alkyl group having a carbon number of 1 to 4, and $R^9$ and $R^{10}$ are a monocyclic or polycyclic cycloalkane structure in which the alicyclic structure is obtained by combining $R^9$ and $R^{10}$ with the carbon atom to which they are bound. Preferably, $L^1$ is a single bond or *—$R^{LA}$O—. Preferred $R^{LA}$ is an alkanediyl group.

Examples of the structural unit (B-1) include structural units represented by the following formulae (3-1) to (3-4) (hereinafter, also referred as "structural unit (B-1-1) to (B-1-4)").

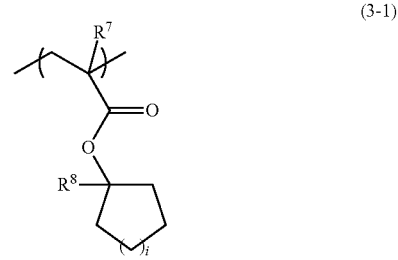

(3-1)

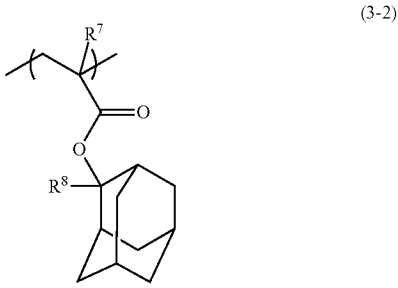

(3-2)

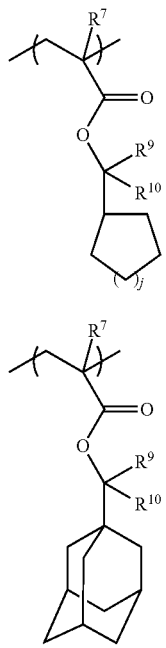

(3-3)

(3-4)

In the above formulae (3-1) to (3-4), $R^7$ to $R^{10}$ have the same meaning as in the above formula (2); and i and j are each independently an integer of 1 to 4. $n_4$ is 0 or 1.

i and j are preferably 1. $R^8$ to $R^{10}$ are preferably a methyl group, an ethyl group, or an iso-propyl group.

Among them, the structural unit (B-1) is preferably the structural unit (B-1-1) or the structural unit (B-1-2), more preferably a structural unit having a cyclopentane structure or a structural unit having an adamantane structure, further preferably a structural unit derived from 1-alkylcyclopentyl (meth)acrylate, a structural unit derived from 2-alkyladamantyl (meth)acrylate, and particularly preferably a structural unit derived from 1-methylcyclohexyl (meth)acrylate or a structural unit derived from 2-ethyladamantyl (meth)acrylate.

The base resin may include one type of the structural unit (B), or two or more types of the structural units (B) in combination.

The lower limit of the content by percent of the structural unit (B) is preferably 5 mol %, more preferably 8 mol %, and further preferably 10 mol % based on the total structural units as the component of the base resin. The upper limit of the content by percent is preferably 90 mol %, more preferably 80 mol %, further preferably 75 mol %, and particularly preferably 70 mol %. By adjusting the content by percent of the structural unit (B) within the ranges, the patternability of the radiation-sensitive resin composition can be further improved.

[Structural Unit (C)]

The structural unit (C) is a structural unit including at least one selected from the group consisting of a lactone structure, a cyclic carbonate structure and a sultone structure. The solubility of the base resin into a developer can be adjusted by further introducing the structural unit (C). As a result, the radiation-sensitive resin composition can provide improved lithography properties such as the resolution. The adhesion between a resist pattern formed from the base resin and a substrate can also be improved.

Examples of the structural unit (C) include structural units represented by the following formulae (T-1) to (T-10).

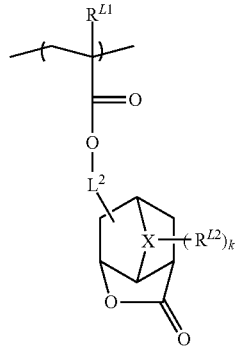

(T-1)

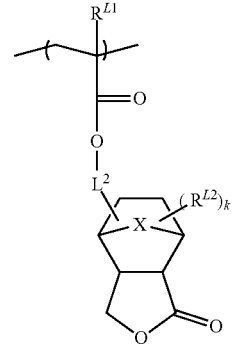

(T-2)

(T-3)

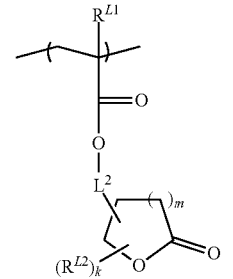

(T-4)

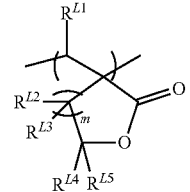

(T-5)

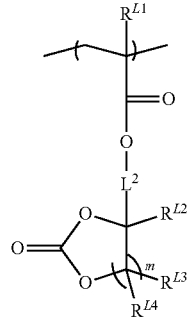

(T-6) 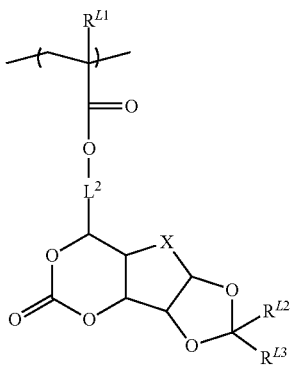

(T-7) 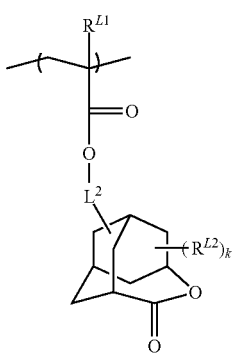

(T-8) 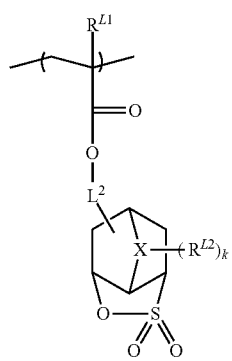

(T-9) 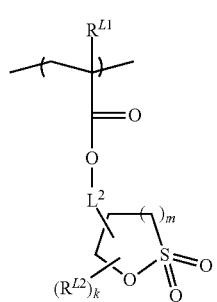

(T-10) 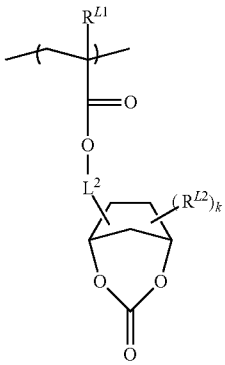

In the above formulae, $R^{L1}$ is a hydrogen atom, a fluorine atom, a methyl group, or a trifluoromethyl group; $R^{L2}$ to $R^{L5}$ are each independently a hydrogen atom, an alkyl group having a carbon number of 1 to 4, a cyano group, a trifluoromethyl group, a methoxy group, a methoxycarbonyl group, a hydroxy group, a hydroxymethyl group, or a dimethylamino group; $R^{L4}$ and $R^{L5}$ may be a divalent alicyclic group having a carbon number of 3 to 8, which is obtained by combining $R^{L4}$ and $R^{L5}$ with the carbon atom to which they are bound. $L^2$ is a single bond, or a divalent linking group; X is an oxygen atom or a methylene group; k is an integer of 0 to 3; and m is an integer of 1 to 3.

Example of the divalent alicyclic group having a carbon number of 3 to 8, which is composed of a combination of $R^{L4}$ and $R^{L5}$ with the carbon atom to which they are bound, includes the divalent alicyclic group having a carbon number of 3 to 8 in the divalent alicyclic group having a carbon number of 3 to 20, which is composed of a combination of the chain hydrocarbon group or the alicyclic hydrocarbon group represented by $R^9$ and $R^{10}$ in the above formula (2) with the carbon atom to which they are bound. One or more hydrogen atoms on the alicyclic group may be substituted with a hydroxy group.

Examples of the divalent linking group represented by $L^2$ as described above include a divalent straight or branched chain hydrocarbon group having a carbon number of 1 to 10; a divalent alicyclic hydrocarbon group having a carbon number of 4 to 12; and a group composed of one or more of the hydrocarbon group thereof and at least one group of —CO—, —O—, —NH— and —S—.

Among them, the structural unit (C) is preferably a group having a lactone structure, more preferably a group having a norbornane lactone structure, and further preferably a group derived from a norbornane lactone-yl (meth)acrylate.

The lower limit of the content by percent of the structural unit (C) is preferably 10 mol %, more preferably 15 mol %, and further preferably 20 mol % based on the total structural units as the component of the base resin. The upper limit of the content by percent is preferably 80 mol %, more preferably 75 mol %, and further preferably 70 mol %. By adjusting the content by percent of the structural unit (C) within the ranges, the radiation-sensitive resin composition can provide improved lithography properties such as the resolution. The adhesion between the formed resist pattern and the substrate can also be improved.

[Structural Unit (D)]

The base resin may also include any other structural unit in addition to the structural units (B) and (C). Example of the other structural unit includes a structural unit (D) having a polar group, provided that the structural unit within the scope of the structural unit (C) is excluded. The base resin can adjust its solubility into the developer by further including the structural unit having a polar group in the resin. As a result, the radiation-sensitive resin composition can provide improved lithography properties such as the resolution. Examples of the polar group include a hydroxy group, a carboxy group, a cyano group, a nitro group, and a sulfonamide group. Among them, a hydroxy group or a carboxy group is preferred, and a hydroxy group is more preferred.

Example of the structural unit (D) having a polar group includes structural units represented by the following formulae.

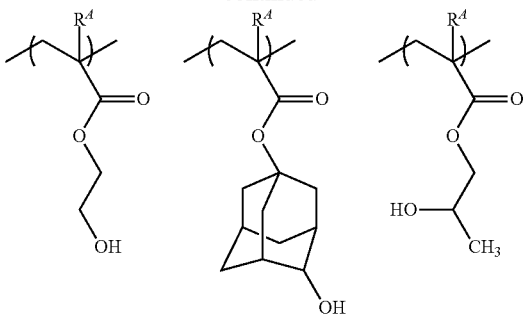

-continued

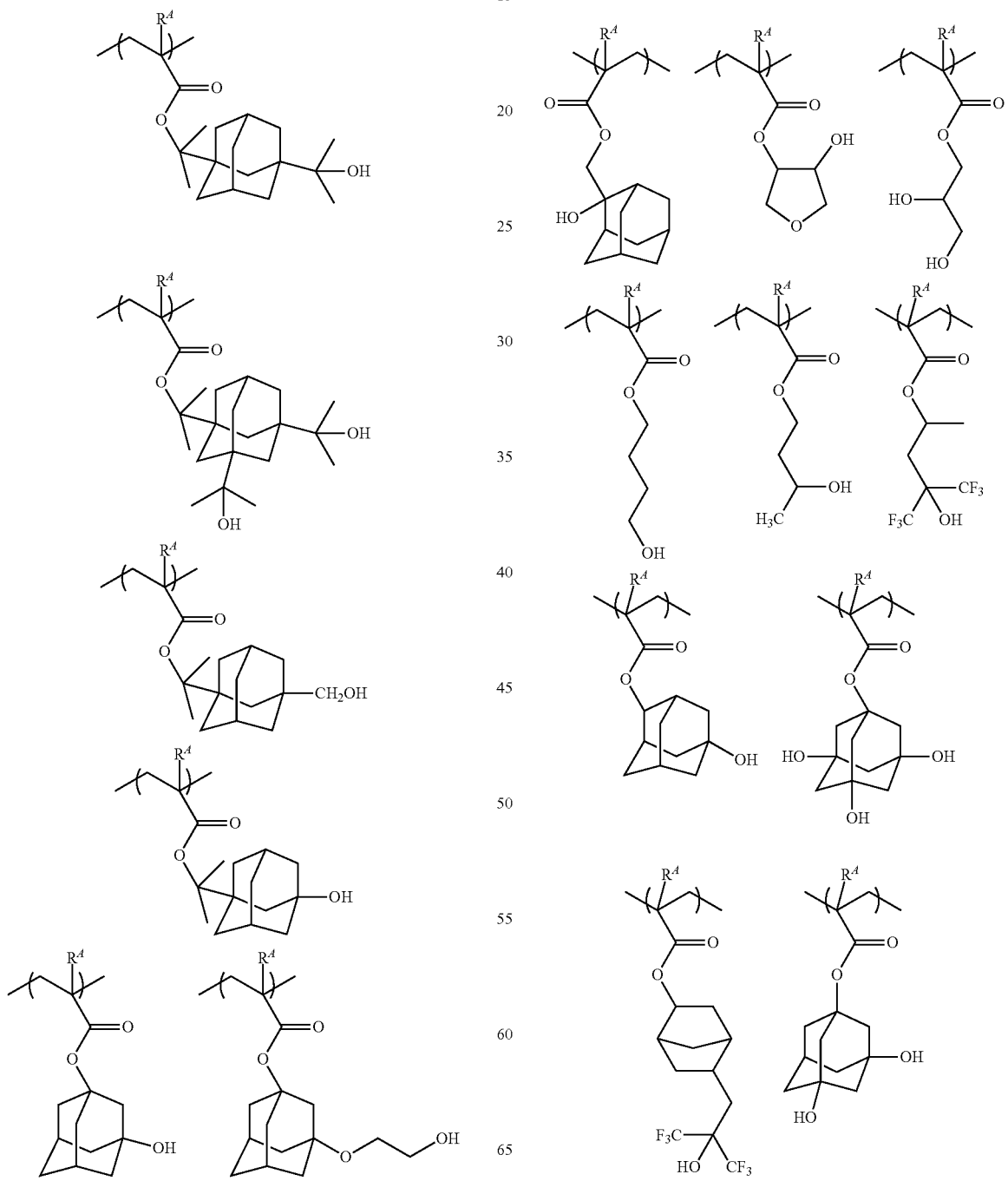

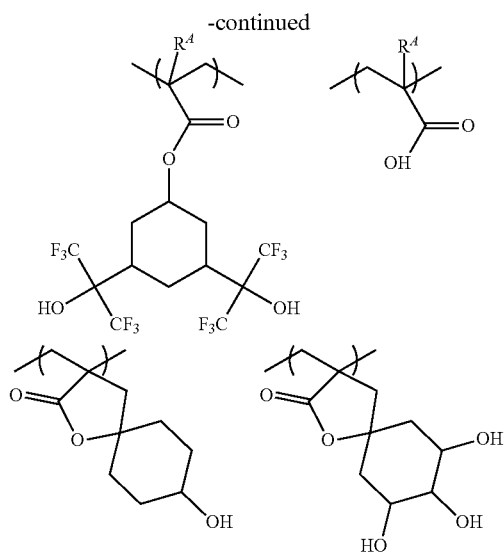

In the above formulae, $R^A$ is a hydrogen atom, a fluorine atom, a methyl group, or a trifluoromethyl group.

When the base resin includes the structural unit (D) having a polar group, the lower limit of the content by percent of the structural unit (D) having a polar group is preferably 5 mol %, more preferably 8 mol %, and further preferably 10 mol % based on the total structural units as the component of the base resin. The upper limit of the content by percent is preferably 50 mol %, more preferably 40 mol %, and further preferably 30 mol %. By adjusting the content by percent of the structural unit having a polar group within the ranges, the radiation-sensitive resin composition can provide improved lithography properties such as the resolution.

[Structural Unit (E)]

The base resin may also include a structural unit including a phenolic hydroxide group (hereinafter, also referred as a "structural unit (E)") as the other structural unit in addition to the structural unit (D) having a polar group. The structural unit (E) contributes to the improvement of the etching resistance and the improvement of the difference in solubility into the developer between the exposed part and the non-exposed part (solubility contrast). In particular, the resin can be suitably applied for a pattern formation by exposing to radiation having a wavelength of 50 nm or less, for example, an electron beam or EUV. In this case, the resin has preferably the structural unit (B) and the structural unit (E).

Examples of the structural unit (E) include a structural unit represented by the following formula (af).

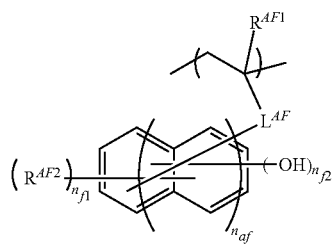

(af)

In the above formula (af), $R^{AF1}$ is a hydrogen atom or a methyl group. $L^{AF}$ is a single bond, —COO—, —O—, or —CONH—. $R^{AF2}$ is a monovalent organic group having 1 to 20 carbon atoms or a halogen atom. $n_{f1}$ is an integer of 0 to 3. When $n_{f1}$ is 2 or 3, a plurality of $R^{AF2}$s may be the same or different. $n_{f2}$ is an integer of 1 to 3. However, $n_{f1}+n_{f2}$ is 5 or less. $n_{af}$ is an integer of 0 to 2.

The $R^{AF1}$ is preferably a hydrogen atom from the viewpoint of the copolymerizability of a monomer giving the structural unit (E).

$L^{AF}$ is preferably a single bond and —COO—.

The organic group in the base resin refers to a group containing at least one carbon atom.

Examples of the monovalent organic group having 1 to 20 carbon atoms, represented by $R^{AF2}$ include a monovalent hydrocarbon group having 1 to 20 carbon atoms, a group containing a divalent hetero atom-containing group between two adjacent carbon atoms or at the end of the atomic bonding side of the hydrocarbon group, and a group obtained by substituting with a monovalent hetero atom-containing group, a part or all of hydrogen atoms contained in the group and the hydrocarbon group.

Examples of the monovalent hydrocarbon group having 1 to carbon atoms, represented by $R^{AF2}$ include: alkyl groups such as a methyl group, an ethyl group, a propyl group, and a butyl group;

alkenyl groups such as an ethenyl group, a propenyl group, and a butenyl group;

chain hydrocarbon groups such as alkynyl groups (such as an ethynyl group, a propynyl group, and a butynyl group);

cycloalkyl groups such as a cyclopropyl group, a cyclopentyl group, a cyclohexyl group, a cyclooctyl group, a norbornyl group, and an adamantyl group;

alicyclic hydrocarbon groups such as cycloalkenyl groups (such as a cyclopropenyl group, a cyclopentenyl group, a cyclohexenyl group, and a norbornenyl group);

aryl groups such as a phenyl group, a tolyl group, a xylyl group, a naphthyl group, and an anthryl group; and aromatic hydrocarbon groups such as aralkyl groups (such as a benzyl group, a phenethyl group, and a naphthylmethyl group).

The $R^{AF2}$ is preferably a chain hydrocarbon group or a cycloalkyl group, more preferably an alkyl group and a cycloalkyl group, and still more preferably a methyl group, an ethyl group, a propyl group, a cyclopentyl group, a cyclohexyl group, a cyclooctyl group, and an adamantyl group.

Examples of the divalent heteroatom-containing group include —O—, —CO—, —CO—O—, —S—, —CS—, —SO$_2$—, —NR'—, and a group obtained by combining two or more of these. Suitable examples of the divalent heteroatom-containing group include a methoxy group, an ethoxy group, and a propoxy group. R' is a hydrogen atom or a monovalent hydrocarbon group.

Examples of the monovalent heteroatom-containing group include halogen atoms such as a fluorine atom, a chlorine atom, a bromine atom, and an iodine atom, a hydroxy group, a carboxy group, a cyano group, an amino group, and a sulfanyl group (—SH).

Examples of the halogen atom include a fluorine atom, a chlorine atom, a bromine atom, and an iodine atom.

The $n_{f1}$ is preferably an integer of 0 to 2, more preferably 0 and 1, and still more preferably 0.

The $n_{f2}$ is preferably 1 and 2, and more preferably 1.

The $n_{af}$ is preferably 0 and 1, and more preferably 0.

The structural unit (E) is preferably a structural unit represented by each of the following formulae (a1-1) to (a1-9), or the like.

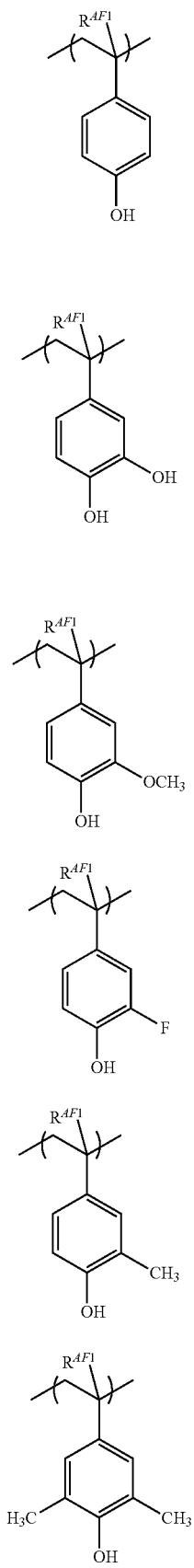

(a1-1)

(a1-2)

(a1-3)

(a1-4)

(a1-5)

(a1-6)

-continued

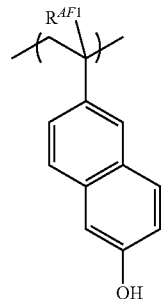 (a1-7)

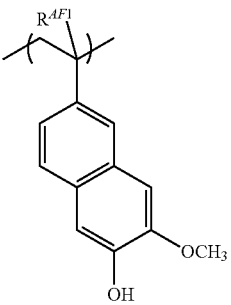 (a1-8)

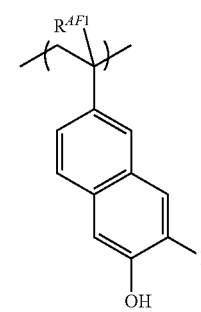 (a1-9)

In the above formulae (a1-1) to (a1-9), $R^{AF1}$ is the same as that in the above formula (af).

Among them, the structural units represented by the above formulae (a1-1) to (a1-7) are preferable, and the structural unit represented by the above formula (a1-1) is more preferable.

The lower limit of the content ratio of the structural unit (E) in the base resin is preferably 10 mol %, more preferably 15 mol %, still more preferably 20 mol %, and particularly preferably 25 mol %, with respect to the total structural units constituting the base resin. The upper limit of the content ratio is preferably 90 mol %, more preferably 80 mol %, and still more preferably 70 mol %. By setting the content ratio of the structural unit (E) within the above range, the CDU performance, LWR performance, and defect-suppression performance of the resist film obtained from the radiation-sensitive resin composition can be further improved.

However, the polymerization of the hydroxystyrene is inhibited by the effect of its phenolic hydroxide group. Therefore, hydroxystyrene is polymerized in a state that the phenolic hydroxide group is preferably protected with a protecting group such as an alkali-dissociable group, and then hydrolyzed for the deprotection of the phenolic hydroxide group to obtain the structural unit (E). The structural unit from which the structural unit (E) is obtained by the hydrolysis is preferably represented by the following formula (af-1).

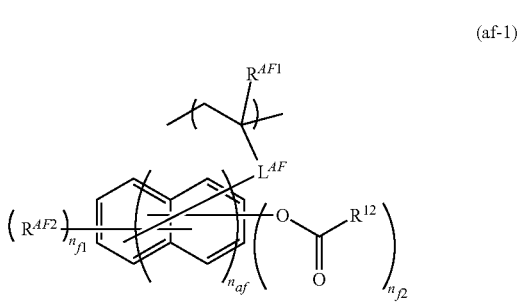

(af-1)

In the above formula (af-1), $R^{AF1}$, $L^{AF}$, $R^{AF2}$, $n_{f1}$, $n_{f2}$ and $n_{af}$ have the same meanings as those in the above formula (af); $R^{12}$ is a monovalent hydrocarbon group having a carbon number of 1 to 20, or an alkoxy group. Example of the monovalent hydrocarbon group having a carbon number of 1 to 20 of $R^{12}$ includes the monovalent hydrocarbon group having a carbon number of 1 to 20 of $R^8$ in the structural unit (B). Examples of the alkoxy group include a methoxy group, an ethoxy group and a tert-butoxy group.

Preferred $R^{12}$ is an alkyl group and an alkoxy group. A methyl group or a tert-butoxy group is more preferred.

(Synthesis Method of Base Resin)

For example, the base resin can be synthesized by polymerizing each monomer for providing each structural unit with a radical polymerization initiator or the like in a suitable solvent.

Examples of the radical polymerization initiator include an azo-based radical initiator, including azobisisobutyronitrile (AIBN), 2,2'-azobis(4-methoxy-2,4-dimethylvaleronitrile), 2,2'-azobis(2-cyclopropylpropanenitrile), 2,2'-azobis (2,4-dimethylvaleronitrile), and dimethyl 2,2'-azobisisobutyrate; and peroxide-based radical initiator, including benzoyl peroxide, t-butyl hydroperoxide, and cumene hydroperoxide. Among them, AIBN or dimethyl 2,2'-azobisisobutyrate is preferred, and AIBN is more preferred. The radical initiator may be used alone, or two or more radical initiators may be used in combination.

Examples of the solvent used for the polymerization include
- alkanes including n-pentane, n-hexane, n-heptane, n-octane, n-nonane, and n-decane;
- cycloalkanes including cyclohexane, cycloheptane, cyclooctane, decalin, and norbornane;
- aromatic hydrocarbons including benzene, toluene, xylene, ethylbenzene, and cumene;
- halogenated hydrocarbons including chlorobutanes, bromohexanes, dichloroethanes, hexamethylenedibromide, and chlorobenzenes;
- saturated carboxylate esters, including ethyl acetate, n-butyl acetate, i-butyl acetate, and methyl propionate;
- ketones including acetone, methyl ethylketone, 4-methyl-2-pentanone, and 2-heptanone;
- ethers including tetrahydrofuran, dimethoxyethanes, and diethoxyethanes; and
- alcohols including methanol, ethanol, 1-propanol, 2-propanol, and 4-methyl-2-pentanol. The solvent used for the polymerization may be used alone, or two or more solvents may be used in combination.

The reaction temperature of the polymerization is typically from 40° C. to 150° C., and preferably from 50° C. to 120° C. The reaction time is typically from 1 hour to 48 hours, and preferably from 1 hour to 24 hours.

The molecular weight of the base resin is not particularly limited, but the weight average molecular weight (Mw) in terms of polystyrene, as measured by gel permeation chromatography (GPC) is preferably 1,000 or more and 50,000 or less, more preferably 2,000 or more and 30,000 or less, and still more preferably 3,000 or more and 20,000 or less. When the base resin of the present embodiment is used in a radiation-sensitive resin composition for ArF exposure, the Mw is more preferably 7,000 or more and 15,000 or less, and particularly preferably 9,000 or more and 13,000 or less. When the base resin of the present embodiment is used in a radiation-sensitive resin composition for EUV exposure, the Mw is more preferably 5,000 or more and 15,000 or less, and particularly preferably 6,000 or more and 11,000 or less. When the Mw of the base resin is less than the lower limit, the heat resistance of the resulting resist film may be deteriorated. When the Mw of the base resin exceeds the above upper limit, the developability of the resist film may be deteriorated.

For the base resin, the ratio of Mw to the number average molecular weight (Mn) as determined by GPC relative to standard polystyrene (Mw/Mn) is typically not less than 1 and not more than 5, preferably not less than 1 and not more than 3, and more preferably not less than 1 and not more than 2.

The Mw and Mn of the resin according to the embodiment of the present invention are amounts measured by using Gel Permeation Chromatography (GPC) with the condition as described below.

GPC column: two G2000HXL, one G3000HXL, and one G4000HXL (all manufactured from Tosoh Corporation)

Column temperature: 40° C.

Eluting solvent: tetrahydrofuran

Flow rate: 1.0 mL/min

Sample concentration: 1.0% by mass

Sample injection amount: 100 μL

Detector: Differential Refractometer

Reference material: monodisperse polystyrene

The content of the base resin is preferably not less than 70% by mass, more preferably not less than 80% by mass, and further preferably not less than 85% by mass based on the total solid content of the radiation-sensitive resin composition.

[Other Resin]

The radiation-sensitive resin composition of this embodiment may include a resin having higher content by mass of fluorine atoms than the base resin as described above (hereinafter, also referred as a "high fluorine-containing resin") as the other resin. When the radiation-sensitive resin composition includes the high fluorine-containing resin, the high fluorine-containing resin can be localized on the surface layer of the resist film compared to the base resin. Therefore, the water repellency of the surface of the resist film can be improved during the immersion exposure. When the immersion exposure is not performed, the elution of the upper part of the pattern is suppressed during development, so that the rectangularity of the pattern can be improved.

The high fluorine-containing resin is preferably one having a structural unit represented by the following formula (5) (hereinafter, also referred as a "structural unit (F)") in addition to at least one of the structural unit (B) and the structural unit (C) in the base resin as described above.

(5)

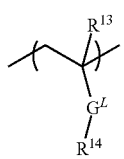

(f-2)

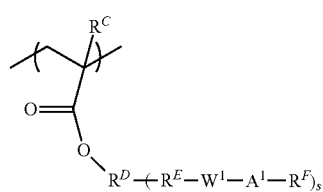

In the above formula (5), $R^{13}$ is a hydrogen atom, a methyl group, or a trifluoromethyl group; G is a single bond, an oxygen atom, a sulfur atom, —COO—, —SO$_2$ONH—, —CONH—, or —OCONH—; $R^{14}$ is a monovalent fluorinated chain hydrocarbon group having a carbon number of 1 to 20, or a monovalent fluorinated alicyclic hydrocarbon group having a carbon number of 3 to 20.

As $R^{13}$ as described above, in terms of the copolymerizability of monomers resulting in the structural unit (F), a hydrogen atom or a methyl group is preferred, and a methyl group is more preferred.

As $G^L$ as described above, in terms of the copolymerizability of monomers resulting in the structural unit (F), a single bond or —COO— is preferred, and —COO— is more preferred.

Example of the monovalent fluorinated chain hydrocarbon group having a carbon number of 1 to 20 represented by $R^{14}$ as described above includes a group in which a part of or all of hydrogen atoms in the straight or branched chain alkyl group having a carbon number of 1 to 20 is/are substituted with a fluorine atom.

Example of the monovalent fluorinated alicyclic hydrocarbon group having a carbon number of 3 to 20 represented by $R^{14}$ as described above includes a group in which a part of or all of hydrogen atoms in the monocyclic or polycyclic hydrocarbon group having a carbon number of 3 to 20 is/are substituted with a fluorine atom.

The $R^{14}$ as described above is preferably a fluorinated chain hydrocarbon group, more preferably a fluorinated alkyl group, and further preferably 2,2,2-trifluoroethyl group, 1,1,1,3,3,3-hexafluoropropyl group and 5,5,5-trifluoro-1,1-diethylpentyl group.

When the high fluorine-containing resin has the structural unit (F), the lower limit of the content by percent of the structural unit (F) is preferably 20 mol %, more preferably 30 mol %, further preferably 35 mol %, and particularly preferably 40 mol % based on the total structural units as the component of the high fluorine-containing resin. The upper limit of the content by percent is preferably 90 mol %, more preferably 85 mol %, and further preferably 80 mol %. By adjusting the content by percent of the structural unit (F) within the ranges, the content by mass percent of fluorine atoms of the high fluorine-containing resin can be suitably adjusted to promote the localization of the high fluorine-containing resin on the surface layer of the resist film. Therefore, the water repellency of the surface of the resist film can be improved during the immersion exposure.

The high fluorine-containing resin may include a structural unit having a fluorine atom represented by the following formula (f-2) (hereinafter, also referred as a "structural unit (G)") in addition to the structural unit (F).

The solubility of the high fluorine-containing resin into an alkaline developing solution can be improved by including the structural unit (G), and thereby prevent from generating the development defect.

The structural unit (G) is classified into two groups: a unit having an alkali soluble group (x); and a unit having a group (y) in which the solubility into the alkaline developing solution is increased by the dissociation by alkali (hereinafter, simply referred as an "alkali-dissociable group"). In both cases of (x) and (y), $R^c$ in the above formula (f-2) is a hydrogen atom, a fluorine atom, a methyl group, or a trifluoromethyl group; $R^D$ is a single bond, a hydrocarbon group having a carbon number of 1 to 20 with the valency of (s+1), a structure in which an oxygen atom, a sulfur atom, —NR$^{dd}$—, a carbonyl group, —COO— or —CONH— is connected to the terminal on $R^E$ side of the hydrocarbon group, or a structure in which a part of hydrogen atoms in the hydrocarbon group is substituted with an organic group having a hetero atom; $R^{dd}$ is a hydrogen atom, or a monovalent hydrocarbon group having a carbon number of 1 to 10; and s is an integer of 1 to 3.

When the structural unit (G) has the alkali soluble group (x), $R^F$ is a hydrogen atom; $A^1$ is an oxygen atom, —COO—* or —SO$_2$O—*; * refers to a bond to $R^F$; $W^1$ is a single bond, a hydrocarbon group having a carbon number of 1 to 20, or a divalent fluorinated hydrocarbon group. When $A^1$ is an oxygen atom, $W^1$ is a fluorinated hydrocarbon group having a fluorine atom or a fluoroalkyl group on the carbon atom connecting to $A^1$. $R^E$ is a single bond, or a divalent organic group having a carbon number of 1 to 20. When s is 2 or 3, a plurality of $R^E$, $W^1$, $A^1$ and $R^F$ may be each identical or different. The affinity of the high fluorine-containing resin into the alkaline developing solution can be improved by including the structural unit (G) having the alkali soluble group (x), and thereby prevent from generating the development defect. As the structural unit (G) having the alkali soluble group (x), particularly preferred is a structural unit in which $A^1$ is an oxygen atom and $W^1$ is a 1,1,1,3,3,3-hexafluoro-2,2-methanediyl group.

When the structural unit (G) has the alkali-dissociable group (y), $R^F$ is a monovalent organic group having carbon number of 1 to 30; $A^1$ is an oxygen atom, —NR$^{aa}$—, —COO—*, or —SO$_2$O—*; $R^{aa}$ is a hydrogen atom, or a monovalent hydrocarbon group having a carbon number of 1 to 10; * refers to a bond to $R^F$; $W^1$ is a single bond, or a divalent fluorinated hydrocarbon group having a carbon number of 1 to 20; $R^E$ is a single bond, or a divalent organic group having a carbon number of 1 to 20. When $A^1$ is —COO—* or —SO$_2$O—*, $W^1$ or $R^F$ has a fluorine atom on the carbon atom connecting to $A^1$ or on the carbon atom adjacent to the carbon atom. When $A^1$ is an oxygen atom, $W^1$ and $R^E$ are a single bond; $R^D$ is a structure in which a carbonyl group is connected at the terminal on $R^E$ side of the hydrocarbon group having a carbon number of 1 to 20; and $R^F$ is an organic group having a fluorine atom. When s is 2 or 3, a plurality of $R^E$, $W^1$, $A^1$ and $R^F$ may be each identical or different. The surface of the resist film is changed from hydrophobic to hydrophilic in the alkaline developing step by including the structural unit (G) having the alkali-dissociable group (y). As a result, the affinity of the high fluorine-containing resin into the alkaline developing solution can be significantly improved, and thereby prevent from generating the development defect more efficiently. As the structural unit (V) having the alkali-dissociable group (y), particularly preferred is a structural unit in which $A^1$ is —COO—*, and $R^F$ or $W^1$, or both is/are a fluorine atom.

In terms of the copolymerizability of monomers resulting in the structural unit (G), $R^c$ is preferably a hydrogen atom or a methyl group, and more preferably a methyl group.

When $R^E$ is a divalent organic group, $R^E$ is preferably a group having a lactone structure, more preferably a group having a polycyclic lactone structure, and further preferably a group having a norbornane lactone structure.

When the high fluorine-containing resin has the structural unit (G), the lower limit of the content by percent of the structural unit (G) is preferably 10 mol %, more preferably 20 mol %, further preferably 30 mol %, and particularly preferably 35 mol % based on the total structural units as the component of the high fluorine-containing resin. The upper limit of the content by percent is preferably 90 mol %, more preferably 75 mol %, and further preferably 60 mol %. By adjusting the content by percent of the structural unit (G) within the ranges, the water repellency of the surface of the resist film can be further improved during the immersion exposure.

The lower limit of Mw of the high fluorine-containing resin is preferably 1,000, more preferably 2,000, further preferably 3,000, and particularly preferably 5,000. The upper limit of Mw is preferably 50,000, more preferably 30,000, further preferably 20,000, and particularly preferably 15,000.

The lower limit of the Mw/Mn of the high fluorine-containing resin is typically 1, and more preferably 1.1. The upper limit of the Mw/Mn is typically 5, preferably 3, more preferably 2, and further preferably 1.7.

The lower limit of the content of the high fluorine-containing resin is preferably 0.1 part by mass, more preferably 1 part by mass, further preferably 1.5 part by mass, and particularly preferably 2 part by mass based on 100 parts by mass of total base resins. The upper limit of the content is preferably 15 parts by mass, more preferably 12 parts by mass, further preferably 10 parts by mass, and particularly preferably 8 parts by mass.

By adjusting the content of the high fluorine-containing resin within the ranges, the high fluorine-containing resin can be localized on the surface layer of the resist film more efficiently. Therefore, the water repellency of the surface of the resist film can be improved during the immersion exposure. The radiation-sensitive resin composition may contain one type of the high fluorine-containing resin, or two or more high fluorine-containing resins in combination.

(Method for Synthesizing High Fluorine-Containing Resin)

The high fluorine-containing resin can be synthesized by the similar method for the base resin as described above.

[Radiation-Sensitive Acid Generator]

The radiation-sensitive acid generator is a component that generates an acid during exposure. The acid generated during exposure is considered to have two functions in the radiation-sensitive resin composition depending on the strength of the acid. Examples of the first function include a function that causes the acid generated during exposure to dissociate an acid dissociable group of each of a structural unit A of the resin and a structural unit (B) (hereinafter, the structural unit A and the structural unit (B) are also collectively referred to as a "structural unit A and the like") when the resin contains the structural unit (B) having the acid dissociable group, to generate a carboxy group or the like.

The radiation-sensitive acid generator having the first function is referred to as a radiation-sensitive acid generator (I). Examples of the second function include a function that suppresses the diffusion of the acid generated from the radiation-sensitive acid generator (I) in the non-exposed part without substantially dissociating the acid dissociable group or the like of the structural unit A of the resin or the like under a pattern formation condition using the radiation-sensitive resin composition. The radiation-sensitive acid generator having the second function is referred to as a radiation-sensitive acid generator (II). The acid generated from the radiation-sensitive acid generator (II) can be said to be relatively weaker (acid having a larger pKa) than the acid generated from the radiation-sensitive acid generator (I). Whether the radiation-sensitive acid generator functions as the radiation-sensitive acid generator (I) or the radiation-sensitive acid generator (II) depends on energy required for the dissociation of the acid-dissociable group of the structural unit A or the like of the resin, and heat energy conditions applied when a pattern is formed using the radiation-sensitive resin composition, and the like. The containing mode of the radiation-sensitive acid generator in the radiation-sensitive resin composition may be a mode in which the radiation-sensitive acid generator is present alone as a compound (released from a polymer), a mode in which the radiation-sensitive acid generator is incorporated as a part of a polymer, or both of these forms, but a mode in which the radiation-sensitive acid generator is present alone as a compound is preferable.

When the radiation-sensitive resin composition contains the radiation-sensitive acid generator (I), the polarity of the resin in the exposed part increases, whereby the resin in the exposed part is soluble in the developer in the case of alkaline aqueous solution development, and is poorly soluble in the developer in the case of organic solvent development.

The radiation-sensitive resin composition contains the radiation-sensitive acid generator (II), whereby a resist pattern having more excellent pattern developability, LWR performance, and CDU performance can be formed from the radiation-sensitive resin composition.

Examples of the radiation-sensitive acid generator include an onium salt compound, a sulfonimide compound, a halogen-containing compound, and a diazoketone compound. Examples of the onium salt compound include a sulfonium salt, a tetrahydrothiophenium salt, an iodonium salt, a phosphonium salt, a diazonium salt, and a pyridinium salt. Among them, a sulfonium salt and an iodonium salt are preferable.

Examples of the acid generated during exposure include acids that generate sulfonic acid, carboxylic acid, and sulfonimide during exposure. Examples of such an acid include (1) a compound in which the carbon atom adjacent to the sulfo group is substituted with one or more fluorine atoms or fluorinated hydrocarbon groups, and (2) a compound in which the carbon atom adjacent to the sulfo group is not substituted with a fluorine atom or a fluorinated hydrocarbon group.

Examples of the carboxylic acid generated during exposure include (3) a compound in which the carbon atom adjacent to the carboxy group is substituted with one or more fluorine atoms or fluorinated hydrocarbon groups, and (4) a compound in which the carbon atom adjacent to the carboxy group is not substituted with a fluorine atom or a fluorinated hydrocarbon group.

Among them, as the radiation-sensitive acid generator (1), a radiation-sensitive acid generator corresponding to the above (1) is preferable, and a radiation-sensitive acid generator having a cyclic structure is particularly preferable. As the radiation-sensitive acid generator (II), a radiation-sensitive acid generator corresponding to the above (2), (3), or (4) is preferable, and a radiation-sensitive acid generator corresponding to the above (2) or (4) is particularly preferable.

These radiation-sensitive acid generators may be used alone or in combination of two or more thereof. The lower limit of the content of the radiation-sensitive acid generator (I) is preferably 1 part by mass, more preferably 2 parts by mass, and still more preferably 3 parts by mass, with respect to 100 parts by mass of the resin, from the viewpoint of securing sensitivity and developability as a resist. The upper limit of the content of the radiation-sensitive acid generator (I) is preferably 30 parts by mass, more preferably parts by mass, and still more preferably 20 parts by mass, with respect to 100 parts by mass of the resin, from the viewpoint of securing transparency to radiation.

[Solvent]

The radiation-sensitive resin composition includes a solvent. The solvent is not particularly limited as long as the solvent can dissolve or disperse at least the resin, the radiation-sensitive acid generator, and optionally an agent such as an acid diffusion controlling agent, if needed.

Examples of the solvent include an alcohol-based solvent, an ether-based solvent, a ketone-based solvent, an amide-based solvent, an ester-based solvent, and a hydrocarbon-based solvent.

Examples of the alcohol-based solvent include:
a monoalcohol-based solvent having a carbon number of 1 to 18, including iso-propanol, 4-methyl-2-pentanol, 3-methoxybutanol, n-hexanol, 2-ethylhexanol, furfuryl alcohol, cyclohexanol, 3,3,5-trimethylcyclohexanol, and diacetone alcohol;
a polyhydric alcohol having a carbon number of 2 to 18, including ethylene glycol, 1,2-propylene glycol, 2-methyl-2,4-pentanediol, 2,5-hexanediol, diethylene glycol, dipropylene glycol, triethylene glycol, and tripropylene glycol; and
a partially etherized polyhydric alcohol-based solvent in which a part of hydroxy groups in the polyhydric alcohol-based solvent is etherized.

Examples of the ether-based solvent include:
a dialkyl ether-based solvent, including diethyl ether, dipropyl ether, and dibutyl ether;
a cyclic ether-based solvent, including tetrahydrofuran and tetrahydropyran;
an ether-based solvent having an aromatic ring, including diphenylether and anisole (methyl phenyl ether); and
an etherized polyhydric alcohol-based solvent in which a hydroxy group in the polyhydric alcohol-based solvent is etherized.

Examples of the ketone-based solvent include:
a chain ketone-based solvent, including acetone, butanone, and methyl-iso-butyl ketone;
a cyclic ketone-based solvent, including cyclopentanone, cyclohexanone, and methylcyclohexanone; and
2,4-pentanedione, acetonylacetone, and acetophenone.

Examples of the amide-based solvent include:
a cyclic amide-based solvent, including N,N'-dimethyl imidazolidinone and N-methylpyrrolidone; and
a chain amide-based solvent, including N-methylformamide, N,N-dimethylformamide, N,N-diethylformamide, acetamide, N-methylacetamide, N,N-dimethylacetamide, and N-methylpropionamide.

Examples of the ester-based solvent include:
a monocarboxylate ester-based solvent, including n-butyl acetate and ethyl lactate;
a partially etherized polyhydric alcohol acetate-based solvent, including diethylene glycol mono-n-butyl ether acetate, propylene glycol monomethyl ether acetate, and dipropylene glycol monomethyl ether acetate;
a lactone-based solvent, including γ-butyrolactone and valerolactone;
a carbonate-based solvent, including diethyl carbonate, ethylene carbonate, and propylene carbonate; and
a polyhydric carboxylic acid diester-based solvent, including propylene glycol diacetate, methoxy triglycol acetate, diethyl oxalate, ethyl acetoacetate, ethyl lactate, and diethyl phthalate.

Examples of the hydrocarbon-based solvent include:
an aliphatic hydrocarbon-based solvent, including n-hexane, cyclohexane, and methylcyclohexane;
an aromatic hydrocarbon-based solvent, including benzene, toluene, di-iso-propylbenzene, and n-amylnaphthalene.

Among them, the ester-based solvent or the ketone-based solvent is preferred. The partially etherized polyhydric alcohol acetate-based solvent, the cyclic ketone-based solvent, or the lactone-based solvent is more preferred. Propylene glycol monomethyl ether acetate, cyclohexanone, or γ-butyrolactone is still more preferred. The radiation-sensitive resin composition may include one type of the solvent, or two or more types of the solvents in combination.

[Other Optional Ingredient]

The radiation-sensitive resin composition may also include any other optional ingredient in addition to the ingredients as described above. Examples of the other optional ingredient include an acid diffusion controlling agent, a localization enhancing agent, a surfactant, an alicyclic backbone-containing compound, and a sensitizer. The other optional ingredient may be used alone, or two or more other optional ingredients may be used in combination.

(Acid Diffusion Controlling Agent)

The radiation-sensitive resin composition may include an acid diffusion controlling agent, if needed. The radiation-sensitive acid generator (I) among the radiation-sensitive acid generator can suitably adopted as the acid diffusion controlling agent. The acid diffusion controlling agent has an effect of controlling the diffusion phenomenon in which an acid resulted from the radiation-sensitive acid generator by the exposure is diffused in the resist film, and of inhibiting undesired chemical reaction in the non-exposed part. The acid diffusion controlling agent can also improve the storage stability of the resulting radiation-sensitive resin composition. The acid diffusion controlling agent can further improve the resolution of the resist pattern and prevent from changing the line width of the resist pattern because of the variation of the pulling and placing time, i.e., the time from the exposure to the developing treatment, and therefore provide the radiation-sensitive resin composition having an improved process stability.

The lower limit of the content of the acid diffusion controlling agent is preferably 0.5 parts by mass, more preferably 0.8 parts by mass, and still more preferably 1 part by mass, with respect to 100 parts by mass of the total radiation-sensitive acid generators. The upper limit of the content is preferably 20 parts by mass, more preferably 15 parts by mass, and still more preferably 10 parts by mass.

By adjusting the content of the acid diffusion controlling agent within the ranges, the radiation-sensitive resin composition can provide improved lithography properties. The radiation-sensitive resin composition may contain one type of the acid diffusion controlling agent, or two or more acid diffusion controlling agents in combination.

(Localization Enhancing Agent)

The localization enhancing agent has an effect of localizing the high fluorine-containing resin on the surface of the resist film more effectively. The added amount of the high fluorine-containing resin can be decreased compared to the traditionally added amount by including the localization enhancing agent in the radiation-sensitive resin composition. The localization enhancing agent can further prevent from eluting the ingredient of the composition from the resist film to an immersion medium and carry out the immersion exposure at higher speed with a high-speed scan, while maintaining the lithography properties of the radiation-sensitive resin composition. As a result, the hydrophobicity of the surface of the resist film can be improved, resulting in the prevention of the defect due to the immersion, for example, the watermark defect. Example of the compound which may be used as the localization enhancing agent includes a low molecular weight compound having a specific dielectric constant of not less than 30 and not more than 200 and a boiling point of 100° C. or more at 1 atm. Specific examples of the compound include a lactone compound, a carbonate compound, a nitrile compound, and a polyhydric alcohol.

Examples of the lactone compound include γ-butyrolactone, valerolactone, mevaloniclactone, and norbornane lactone.

Examples of the carbonate compound include propylene carbonate, ethylene carbonate, butylene carbonate, and vinylene carbonate.

Example of the nitrile compound includes succinonitrile.

Example of the polyhydric alcohol includes glycerine.

The lower limit of the content of the localization enhancing agent is preferably 10 parts by mass, more preferably 15 parts by mass, further preferably 20 parts by mass, and more further preferably 25 parts by mass based on 100 parts by mass of total resins in the radiation-sensitive resin composition. The upper limit of the content is preferably 300 parts by mass, more preferably 200 parts by mass, further preferably 100 parts by mass, and more further preferably 80 parts by mass. The radiation-sensitive resin composition may include one type of the localization enhancing agent, or two or more types of localization enhancing agents in combination.

(Surfactant)

The surfactant has an effect of improving the coating properties, the striation, and the developability of the composition. Examples of the surfactant include a nonionic surfactant, including polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate. Examples of the surfactant which is commercially available include KP341 (manufactured by Shin-Etsu Chemical Co., Ltd.), POLYFLOW No. 75, POLYFLOW No. 95 (all manufactured by Kyoeisha Chemical Co., Ltd.), EFTOP EF301, EFTOP EF303, EFTOP EF352 (all manufactured by Tokem Products), Megafac F171, Megafac F173 (all manufactured by DIC), Fluorad FC430, Fluorad FC431 (all manufactured by Sumitomo 3M Limited), AsahiGuard AG710, Surflon S-382, Surflon SC-101, Surflon SC-102, Surflon SC-103, Surflon SC-104, Surflon SC-105, Surflon SC-106 (all manufactured by Asahi Glass Co., Ltd.). The content of the surfactant in the radiation-sensitive resin composition is typically not more than 2 parts by mass based on 100 parts by mass of total resins.

(Alicyclic Backbone-Containing Compound)

The alicyclic backbone-containing compound has an effect of improving the dry etching resistance, the shape of the pattern, the adhesiveness between the substrate, and the like.

Examples of the alicyclic backbone-containing compound include:

adamantane derivatives, including 1-adamantane carboxylic acid, 2-adamantanone, and t-butyl 1-adamantane carboxylate;

deoxycholic acid esters, including t-butyl deoxycholate, t-butoxycarbonylmethyl deoxycholate, and 2-ethoxyethyl deoxycholate;

lithocholic acid esters, including t-butyl lithocholate, t-butoxycarbonylmethyl lithocholate, and 2-ethoxyethyl lithocholate; and 3-[2-hydroxy-2,2-bis(trifluoromethyl)ethyl]tetracyclo[4.4.0.1 2,5.17,10]dodecane, and 2-hydroxy-9-methoxycarbonyl-5-oxo-4-oxa-tricyclo[4.2.1.03,7]nonane. The content of the alicyclic backbone-containing compound in the radiation-sensitive resin composition is typically not more than 5 parts by mass based on 100 parts by mass of total resins.

(Sensitizer)

The sensitizer shows an action of increasing the production of the acid, for example, from the radiation-sensitive acid generator, and has an effect of improving the "apparent sensitivity" of the radiation-sensitive resin composition.

Examples of the sensitizer include carbazoles, acetophenones, benzophenones, naphthalenes, phenols, biacetyl, eosin, rose bengal, pyrenes, anthracenes, and phenothiazines. The sensitizer may be used alone, or two or more sensitizers may be used in combination. The content of the sensitizer in the radiation-sensitive resin composition is typically not more than 2 parts by mass based on 100 parts by mass of total resins.

<Method for Preparing Radiation-Sensitive Resin Composition>

For example, the radiation-sensitive resin composition can be prepared by mixing the resin, the radiation-sensitive acid generator, optionally the acid diffusion controlling agent, the high fluorine-containing resin, and the solvent in a predetermined ratio. After mixing, the radiation-sensitive resin composition is preferably filtered, for example, through a membrane filter having a pore size of about 0.05 μm. The solid concentration of the radiation-sensitive resin composition is typically from 0.1% by mass to 50% by mass, preferably from 0.5% by mass to 30% by mass, and more preferably from 1% by mass to 20% by mass.

<Method for Forming Resist Pattern>

The method for forming a resist pattern includes the steps of:

forming a resist film from the radiation-sensitive resin composition (hereinafter, also referred as a "resist film forming step");

exposing the resist film (hereinafter, also referred as a "exposing step"); and developing the exposed resist film (hereinafter, also referred as a "developing step").

According to the method for forming a resist pattern, the resist pattern can be formed having an improved resolution, the rectangularity of the cross-section shape, LWR properties, depth of focus, MEEF properties, and the shrinkage control of the resist film during PEB. Each steps will be described below.

[Resist Film Forming Step]

In this step, a resist film is formed from the radiation-sensitive resin composition. Examples of the substrate on which the resist film is formed include one traditionally known in the art, including a silicon wafer, silicon dioxide, and a wafer coated with aluminum. An organic or inorganic antireflection film may be formed on the substrate, as disclosed in JP-B-06-12452 and JP-A-59-93448.

Examples of the applicating method include a rotary coating (spin coating), flow casting, and roll coating. After applicating, a prebake (PB) may be carried out in order to evaporate the solvent in the film, if needed. The temperature of PB is typically from 60° C. to 140° C., and preferably from 80° C. to 120° C. The duration of PB is typically from 5 seconds to 600 seconds, and preferably from 10 seconds to 300 seconds. The thickness of the resist film formed is preferably from 10 nm to 1,000 nm, and more preferably from 10 nm to 500 nm.

When the immersion exposure is carried out, irrespective of presence of a water repellent polymer additive such as the high fluorine-containing resin in the radiation-sensitive resin composition, the formed resist film may have a protective film for the immersion which is not soluble into the immersion liquid on the film in order to prevent a direct contact between the immersion liquid and the resist film. As the protective film for the immersion, a solvent-removable protective film that is removed with a solvent before the developing step (for example, see JP-A-2006-227632); or a developer-removable protective film that is removed during the development of the developing step (for example, see WO2005-069076 and WO2006-035790) may be used. In terms of the throughput, the developer-removable protective film is preferably used.

When the subsequent exposing step is carried out by a radiation having a wavelength of 50 nm or less, the resin having the structural units (I) and (III) as the base resin is preferably used in the composition.

[Exposing Step]

In this step, the resist film formed in the resist film forming step is exposed by irradiating with a radioactive ray through a photomask (optionally through an immersion medium such as water). Examples of the radioactive ray used for the exposure include visible ray, ultraviolet ray, far ultraviolet ray, extreme ultraviolet ray (EUV); an electromagnetic wave including X ray and γ ray; an electron beam; and a charged particle radiation such as a ray. Among them, far ultraviolet ray, an electron beam, or EUV is preferred. ArF excimer laser light (wavelength is 193 nm), KrF excimer laser light (wavelength is 248 nm), an electron beam, or EUV is more preferred. ArF excimer laser light or EUV is further preferred.

When the exposure is carried out by immersion exposure, examples of the immersion liquid include water and fluorine-based inert liquid. The immersion liquid is preferably a liquid which is transparent with respect to the exposing wavelength, and has a minimum temperature factor of the refractive index so that the distortion of the light image reflected on the film becomes minimum. However, when the exposing light source is ArF excimer laser light (wavelength is 193 nm), water is preferably used because of the ease of availability and ease of handling in addition to the above considerations. When water is used, a small proportion of an additive that decreases the surface tension of water and increases the surface activity may be added. Preferably, the additive can not dissolve the resist film on the wafer and can neglect an influence on an optical coating at an under surface of a lens. The water used is preferably distilled water.

After the exposure, post exposure bake (PEB) is preferably carried out to promote the dissociation of the acid-dissociable group in the resin by the acid generated from the radiation-sensitive acid generator with the exposure in the exposed part of the resist film. The difference of solubility into the developer between the exposed part and the non-exposed part is generated by the PEB. The temperature of PEB is typically from 50° C. to 180° C., and preferably from 80° C. to 130° C. The duration of PEB is typically from 5 seconds to 600 seconds, and preferably from 10 seconds to 300 seconds.

[Developing Step]

In this step, the resist film exposed in the exposing step is developed. By this step, the predetermined resist pattern can be formed. After the development, the resist pattern is washed with a rinse solution such as water or alcohol, and the dried, in general.

Examples of the developer used for the development include, in the alkaline development, an alkaline aqueous solution obtained by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethyl ammonium hydroxide (TMAH), pyrrole, piperidine, choline, 1,8-diazabicyclo-[5.4.0]-7-undecene, 1,5-diazabicyclo-[4.3.0]-5-nonene. Among them, an aqueous TMAH solution is preferred, and 2.38% by mass of aqueous TMAH solution is more preferred.

In the case of the development with organic solvent, examples of the solvent include an organic solvent, including a hydrocarbon-based solvent, an ether-based solvent, an ester-based solvent, a ketone-based solvent, and an alcohol-based solvent; and a solvent containing an organic solvent. Examples of the organic solvent include one, two or more solvents listed as the solvent for the radiation-sensitive resin composition. Among them, an ester-based solvent or a ketone-based solvent is preferred. The ester-based solvent is preferably an acetate ester-based solvent, and more preferably n-butyl acetate or amyl acetate. The ketone-based solvent is preferably a chain ketone, and more preferably 2-heptanone. The content of the organic solvent in the developer is preferably not less than 80% by mass, more preferably not less than 90% by mass, further preferably not less than 95% by mass, and particularly preferably not less than 99% by mass. Examples of the ingredient other than the organic solvent in the developer include water and silicone oil.

Examples of the developing method include a method of dipping the substrate in a tank filled with the developer for a given time (dip method); a method of developing by putting and leaving the developer on the surface of the substrate with the surface tension for a given time (paddle method); a method of spraying the developer on the surface of the substrate (spray method); and a method of injecting the developer while scanning an injection nozzle for the developer at a constant rate on the substrate rolling at a constant rate (dynamic dispense method).

Second Embodiment

The present invention relates, in one embodiment, to a compound represented by the following formula (I) (hereinafter, also referred to as a "compound (I)").

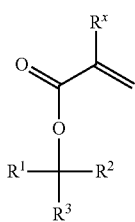

(I)

In the above formula (I), $R^x$ is a hydrogen atom, a fluorine atom, a methyl group, or a trifluoromethyl group.

$R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with a carbon atom to which the groups are bonded.

$R^3$ represents a monovalent alicyclic hydrocarbon group having 4 to 20 carbon atoms and containing a fluorine atom.

Provided that in $R^1$ and $R^2$, no fluorine atom is bonded to carbon atoms located at α-, β- and γ-positions of the carbon atom to which $R^1$ and $R^2$ are bonded.

In $R^3$, no fluorine atom is bonded to carbon atoms located at α- and β-positions of a carbon atom to which $R^3$ is bonded.

The compound (I) has the specific partial structure represented by the above formula (I), whereby the use of the compound (I) as a monomer makes it possible to suitably provide a highly functional material (resin or the like) having a structural unit derived from the compound (I). Therefore, as the specific partial structure in the present embodiment, the specific partial structure represented by the above formula (1) in the first embodiment can be suitably employed. As the structural unit derived from the compound (I), the structural unit (A) in the first embodiment can be suitably employed.

Third Embodiment

The present invention relates, in one embodiment, to a compound represented by the following formula (i) (hereinafter, also referred to as a "compound (i)").

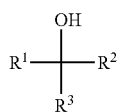

(i)

In the above formula (i), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with a carbon atom to which the groups are bonded.

$R^3$ represents a monovalent alicyclic hydrocarbon group having 4 to 20 carbon atoms and containing a fluorine atom.

Provided that in $R^1$ and $R^2$, no fluorine atom is bonded to carbon atoms located at α-, β- and γ-positions of the carbon atom to which $R^1$ and $R^2$ are bonded.

In $R^3$, no fluorine atom is bonded to carbon atoms located at α- and β-positions of a carbon atom to which $R^3$ is bonded.

Since the compound (i) has the specific structure represented by the above formula (i), a monomer for forming a highly functional material (that is, the compound (I)) can be efficiently produced by causing the esterification reaction of the compound (i) with, for example, a polymerizable group-containing carboxylic acid compound or a derivative thereof to proceed. Therefore, in the above formula (i), as $R^1$, $R^2$, and $R^3$, the same groups as those of the above formula (1) in the first embodiment can be suitably employed.

[Method for Synthesizing Compound (i) and Compound (I)]

A method for synthesizing the compound (i) and the compound (I) is not particularly limited, but a procedure shown by the following scheme can be suitably employed.

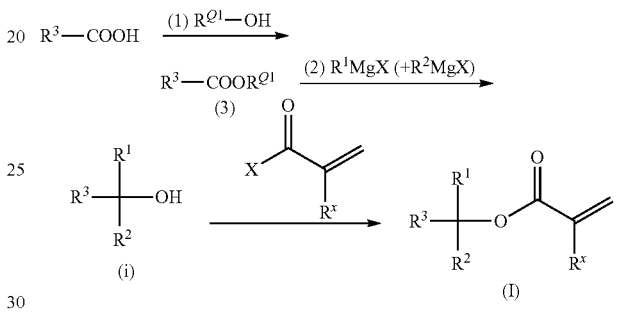

First, an ester compound is produced by reacting a carboxylic acid having a structure corresponding to $R^3$ in the above formula (1) with an alcohol. Subsequently, the ester compound is reacted with a Grignard reagent having a structure corresponding to $R^1$ (and $R^2$), whereby the compound (i) that is a tertiary alcohol compound can be synthesized. Furthermore, the compound (I) can be synthesized by reacting the compound (i) with an acyl halide having a polymerizable group to form an ester bond.

EXAMPLES

Hereinafter, the present invention will be specifically described with reference to Examples, but the present invention is not limited to these Examples. Methods for measuring various physical property values will be described below.

[Measurement of Weight Average Molecular Weight (Mw), Number Average Molecular Weight (Mn) and Dispersity (Mw/Mn)]

The Mw and Mn of the resin were measured by Gel Permeation Chromatography (GPC) with GPC columns manufactured by Tosoh Corporation (two G2000HXLs, one G3000HXL, and one G4000HXL) under the analysis condition as described below, and the dispersity (Mw/Mn) was calculated by the measurement results of Mw and Mn: flow rate: 1.0 mL/min; eluting solvent: tetrahydrofuran; column temperature: 40° C.; and reference material: monodisperse polystyrene.

[$^1$H-NMR Analysis and $^{13}$C-NMR Analysis]

Measurement was performed with use of "JNM-Delta 400" manufactured by JEOL Ltd.

<Synthesis of Resin>

Among the monomers used in the synthesis of the resins in Examples, the structure of the monomer having the partial structure represented by the above formula (1) (that is, the compound (I)) will be shown below. In the following Synthesis Examples, unless otherwise specified, parts by mass means a value assuming that the total mass of the used monomers is 100 parts by mass, and mol % means a value assuming that the total mole number of the used monomers is 100 mol %. The present invention is not limited to the following structural units.

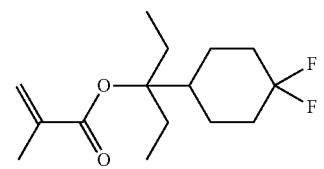
(M-1)

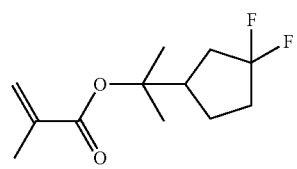
(M-2)

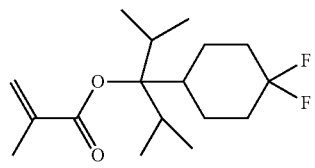
(M-3)

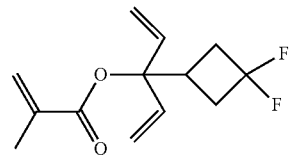
(M-4)

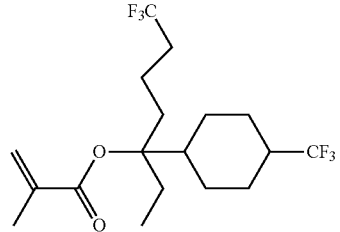
(M-5)

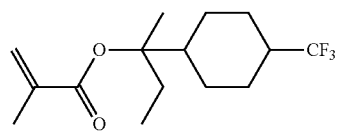
(M-6)

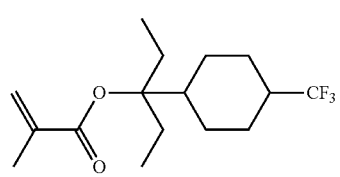
(M-7)

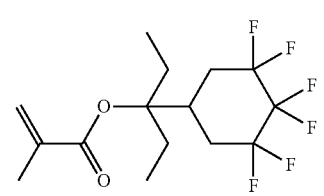
(M-8)

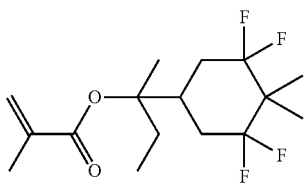
(M-9)

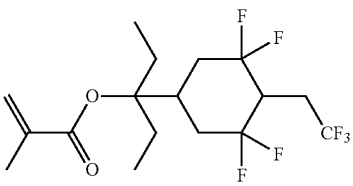
(M-10)

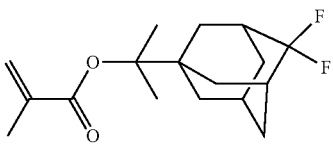
(M-11)

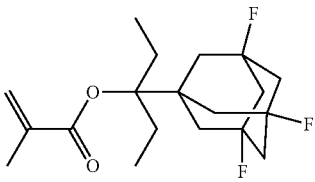
(M-12)

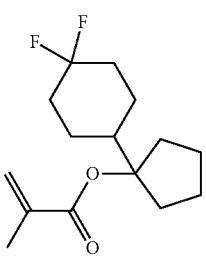
(M-13)

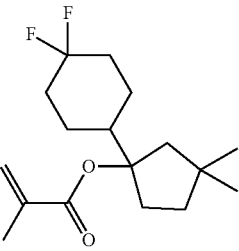
(M-14)

Among the monomers used in the synthesis of the resins in Examples and Comparative Examples, the structures of monomers other than the monomer having the partial structure represented by the above formula (1) will be shown.

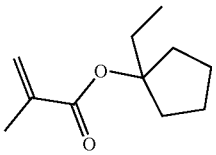
(M-16)

-continued
(M-17)
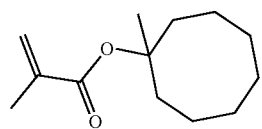
(M-18)
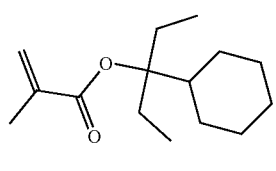
(M-19)
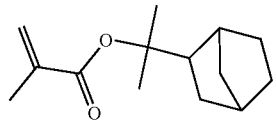
(M-20)
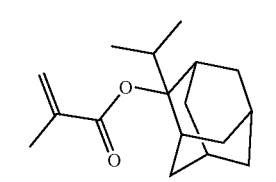
(M-21)
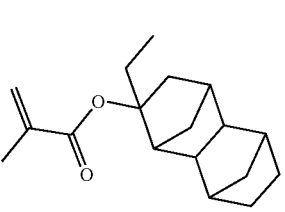
(M-22)
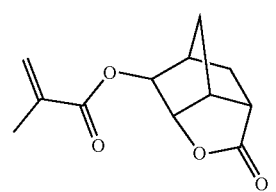
(M-23)
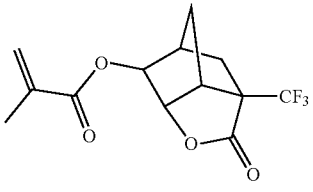
(M-24)
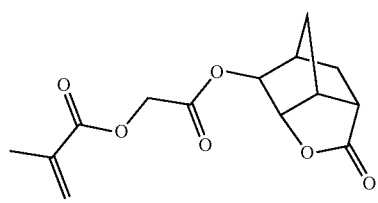
(M-25)
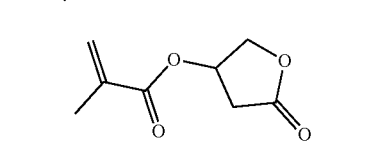
-continued
(M-26)
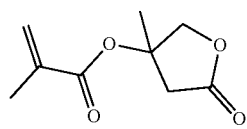
(M-27)
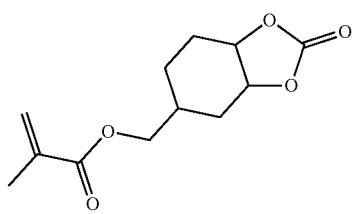
(M-28)
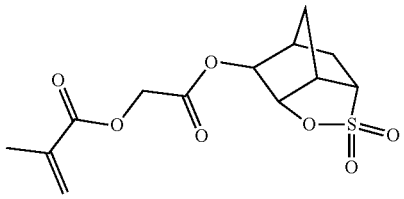
(M-29)
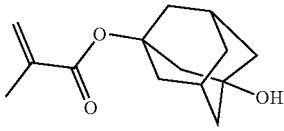
(M-30)
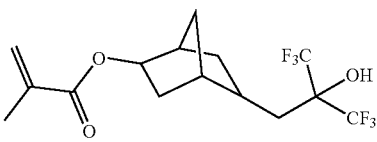
(M-31)
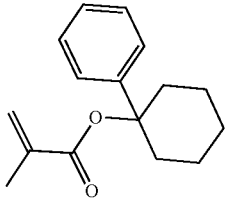
(M-32)
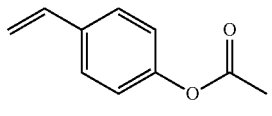
(M-33)
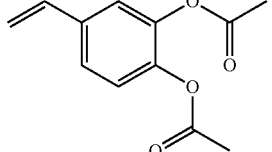
(M-34)
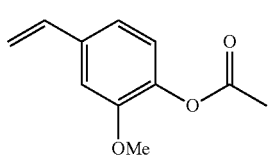

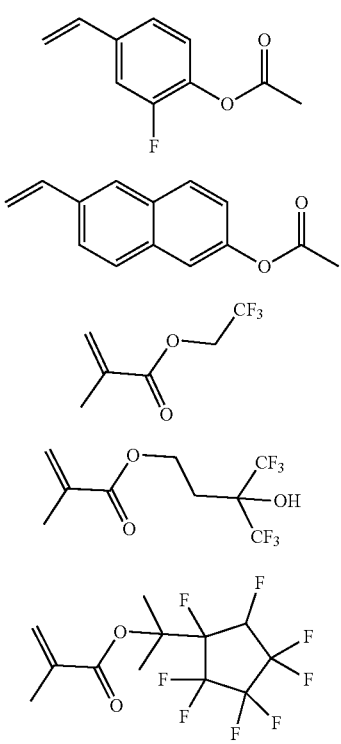

(M-35)
(M-36)
(M-37)
(M-38)
(M-39)

<Method for Synthesizing Monomer Having Partial Structure Represented by Above Formula (1) (Compound (I))>

The monomer (M-1) having a partial structure represented by the above formula (1) was synthesized by the following procedure. Monomers (M-2) to (M-14) were also synthesized in the same manner as in the method for synthesizing the monomer (M-1).

Synthesis Example 1: Synthesis of Monomer (M-1)

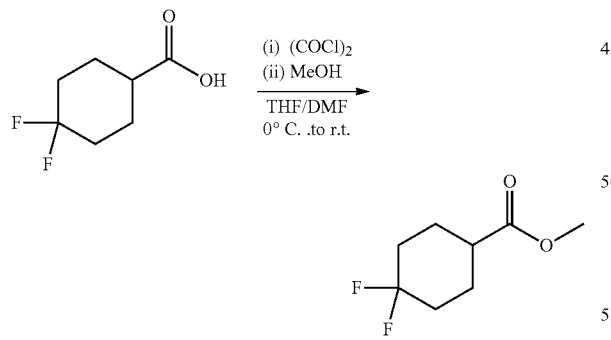

4,4 Difluorocyclohexane-1-carboxylic acid (40.22 g (0.245 mol)) was weighed in a 1-L recovery flask, and dissolved in a mixed solution of tetrahydrofuran (245 mL) and dimethylformamide (1 mL). After the solution was cooled to 0° 37.32 g (0.294 mol) of oxalyl dichloride was added dropwise to the solution at a rate not exceeding 10° C., followed by stirring at room temperature for 0.5 hours after the completion of the dropwise addition. Then, the solution was cooled to 0° C., and methanol (10 mL) was then added dropwise to the solution, followed by stirring at room temperature for 1 hour after completion of the dropwise addition. After the completion of the reaction, the resulting solution was quenched with a saturated aqueous sodium bicarbonate solution, extracted with ethyl acetate, concentrated under reduced pressure, and purified by column chromatography to obtain 39.2 g of methyl 4,4-difluorocyclohexane-1-carboxylate (yield: 90%).

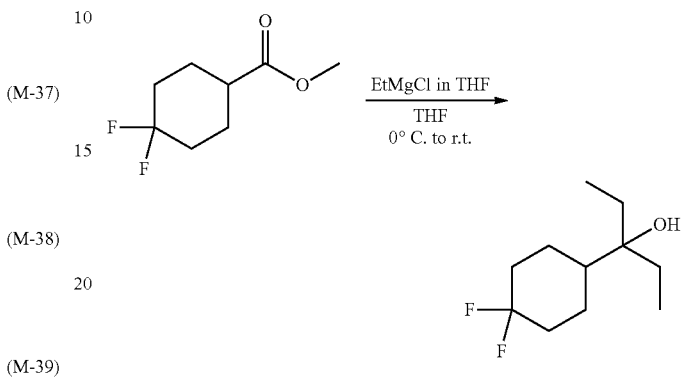

Methyl 4,4-difluorocyclohexane-1-carboxylate (39.2 g (0.22 mol)) was weighed in a 2-L recovery flask, and dissolved in tetrahydrofuran (70 mL). The solution was cooled to 0° C., and then 480 mL of a tetrahydrofuran solution (1.0 M) of ethyl magnesium chloride was added dropwise thereto. After the completion of the reaction, the resulting solution was quenched with a saturated aqueous ammonium chloride solution, extracted with ethyl acetate, concentrated under reduced pressure, and purified by column chromatography to obtain 35.2 g of 3-(4,4-difluorocyclohexyl)pentane-3-ol (yield: 78%).

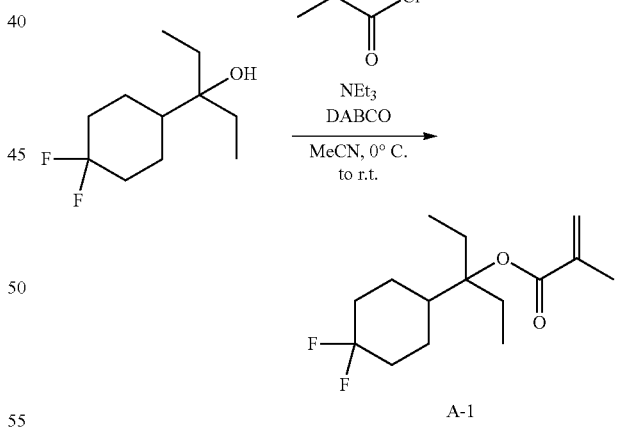

A-1

3-(4,4-Difluorocyclohexyl)pentane-3-ol (35.21 g (0.171 mol)), triethylamine (25.91 g (0.256 mol)), and 1,4-diazabicyclo[2.2.2]octane (5.74 g (0.051 mol)) were weighed in a 500-mL recovery flask, and dissolved in 170 mL of acetonitrile. The solution was cooled to 0° C., and then 26.76 g (0.256 mol) of methacryloyl chloride was added dropwise thereto. After the completion of the dropwise addition, the solution was stirred at room temperature for 24 hours. After the completion of the reaction, the resulting solution was quenched with a saturated aqueous ammonium chloride solution, extracted with ethyl acetate, and concentrated under reduced pressure. The resulting residue was purified by column chromatography to obtain 11.41 g of a monomer (M-1) (yield: 71%).

<Method for Synthesizing Resin>

Synthesis Example 1: Synthesis of Resin (P-1)

The compound (M-1), a compound (M-16), a compound (M-22), and a compound (M-29) as monomers were dissolved in 2-butanone (200 parts by mass with respect to the total amount of monomers) at a molar ratio of 20/30/35/10. Azobisisobutyronitrile (AIBN) (2 mol %) as an initiator was added thereto to prepare a monomer solution. 2-butanone (100 parts by mass) was placed in a reaction vessel, and the reaction vessel was purged with nitrogen gas for 30 minutes. The temperature in the reaction vessel was set at 80° C., and the monomer solution was added dropwise to the reaction vessel under stirring for 3 hours. The polymerization reaction was performed for 6 hours with the start of the dropwise addition as the start time of the polymerization reaction. After the completion of the polymerization reaction, the polymerization solution was cooled with water to 30° C. or lower. The cooled polymerization solution was charged into methanol (2,000 parts by mass), and a precipitated white powder was separated by filtration. The filtered white powder was washed twice with methanol (400 parts by mass), then filtered and dried at 60° C. for 15 hours to obtain a white powdery resin (P-1) in a good yield. The Mw of the resulting resin (P-1) was 9,700, and the Mw/Mn was 1.35. As a result of $^{13}$C-NMR analysis, the content rate of the structural unit derived from the compound (M-1): the structural unit derived from the compound (M-16): the structural unit derived from the compound (M-22): the structural unit derived from the compound (M-29) was 18:30:37:15 (mol %).

[Synthesis Examples 2 to 17, 24, 29, and 30] (Synthesis of Resins (P-2) to (P-17), (P-24), (P-29), and (P-30))

Resins (P-2) to (P-17), (P-24), (P-29), and (P-30) each containing a predetermined amount of monomer shown in Table 1 were obtained in the same manner as in Synthesis Example 1. The Mw and Mw/Mn of each of the resulting resins, and the content rate of the structural unit derived from each of the monomers in each of the resins are shown together in Table 1.

Synthesis Example 18: Synthesis of Resin (P-18)

The compound (M-1), the compound (M-16), and a compound (M-32) as monomers were dissolved in 1-methoxy-2-propanol (200 parts by mass with respect to the total amount of monomers) at a molar ratio of 20/35/45. Next, 4 mol % of azobisisobutyronitrile as an initiator was added into the total of the monomers to prepare a monomer solution. Meanwhile, 1-methoxy-2-propanol (100 parts by mass with respect to the total amount of monomers) was added into an empty reaction vessel, and heated to 85° C. while being stirred. Next, the monomer solution prepared above was added dropwise thereto over 3 hours, followed by further heating at 85° C. for 3 hours to perform a polymerization reaction for a total of 6 hours. After the completion of the polymerization reaction, the polymerization solution was cooled to room temperature. The cooled polymerization solution was charged into hexane (500 parts by mass with respect to the polymerization solution), and a precipitated white powder was separated by filtration. The white powder separated by filtration was washed twice with 100 parts by mass of hexane relative to the polymerization solution, then separated by filtration, and dissolved in 1-methoxy-2-propanol (300 parts by mass). Next, methanol (500 parts by mass), triethylamine (50 parts by mass), and ultrapure water (10 parts by mass) were added to the resulting solution, and a hydrolysis reaction was performed at 70° C. for 6 hours under stirring. After the completion of the reaction, the remaining solvent was distilled off, and the resulting solid was dissolved in acetone (100 parts by mass). The resulting solution was added dropwise into 500 parts by mass of water to permit the coagulation of the resin. The resulting solid was separated by filtration. The solid was dried at 50° C. for 12 hours to synthesize a white powdery resin (P-18). The Mw of the resulting resin (P-18) was 6,800, and the Mw/Mn was 1.59. As a result of $^{13}$C-NMR analysis, the content rate of the structural unit derived from the compound (M-1): the structural unit derived from the compound (M-16): the structural unit derived from the compound (M-32) was 18:35:47 (mol %).

Synthesis Examples 19 to 23, 25 to 28, and 31 and 32

(Synthesis of Resins (P-19) to (P-23), (P-25) to (P-28), and (P-31) and (P-32))

Resins (P-19) to (P-23), (P-25) to (P-28), and (P-31) and (P-32) each containing a predetermined amount of monomer shown in Table 1 were obtained in the same manner as in Synthesis Example 18. The Mw and Mw/Mn of each of the resulting resins, and the content rate of the structural unit derived from each of the monomers in each of the resins are shown together in Table 1.

TABLE 1

| | | Blending Amount of Compound Corresponding to Each Structural Unit (mol %) | | | | | | | | | Comparative Structural Unit | | Content Rate of Each Structural Unit in Polymer (mol %) | | | | | Physical Property Value | |
|---|---|---|---|---|---|---|---|---|---|---|---|---|---|---|---|---|---|---|---|
| | | Structural Unit (A) | | Structural Unit (B) | | Structural Unit (C) | | Structural Unit (D) | | Structural Unit (E) | | | | Structural Unit (A) | Structural Unit (B) | Structural Unit (C) | Structural Unit (D) | Structural Unit (E) | Comparative Structural Unit | Mw | Mw/Mn |
| | Resin | Type | Blending Amount | Type | Blending Amount | Type | Blending Amount | Type | Blending Amount | Type | Blending Amount | Type | Blending Amount | | | | | | | | |
| Synthesis Example 1 | P-1 | M-1 | 20 | M-16 | 30 | M-22 | 35 | M-29 | 10 | — | — | — | — | 18 | 30 | 37 | 15 | — | — | 9700 | 1.35 |
| Synthesis Example 2 | P-2 | M-2 | 25 | M-21 | 20 | M-23 | 55 | — | — | — | — | — | — | 26 | 17 | 57 | — | — | — | 9400 | 1.44 |
| Synthesis Example 3 | P-3 | M-3 | 15 | M-16 | 40 | M-24 | 45 | — | — | — | — | — | — | 11 | 40 | 49 | — | — | — | 10900 | 1.42 |
| Synthesis Example 4 | P-4 | M-4 | 35 | M-20 | 25 | M-26 | 40 | — | — | — | — | — | — | 31 | 25 | 44 | — | — | — | 9600 | 1.48 |
| Synthesis Example 5 | P-5 | M-5 | 10 | M-18 | 50 | M-27 | 40 | — | — | — | — | — | — | 6 | 51 | 43 | — | — | — | 9800 | 1.45 |
| Synthesis Example 6 | P-6 | M-6 | 25 | M-16 | 25 | M-25 | 50 | — | — | — | — | — | — | 23 | 23 | 54 | — | — | — | 9800 | 1.47 |
| Synthesis Example 7 | P-7 | M-7 | 15 | M-19 | 50 | M-22 | 35 | — | — | — | — | — | — | 14 | 46 | 40 | — | — | — | 8700 | 1.46 |
| Synthesis Example 8 | P-8 | M-8 | 5 | M-17 | 40 | M-28 | 45 | M-30 | 10 | — | — | — | — | 5 | 37 | 48 | 11 | — | — | 8500 | 1.44 |
| Synthesis Example 9 | P-9 | M-9 | 20 | M-16 | 35 | M-28 | 45 | — | — | — | — | — | — | 18 | 32 | 49 | — | — | — | 8700 | 1.39 |
| Synthesis Example 10 | P-10 | M-10 | 10 | M-18 | 40 | M-26 | 50 | — | — | — | — | — | — | 9 | 37 | 54 | — | — | — | 8900 | 1.51 |
| Synthesis Example 11 | P-11 | M-11 | 20 | M-16 | 45 | M-23 | 35 | — | — | — | — | — | — | 18 | 41 | 40 | — | — | — | 8800 | 1.61 |
| Synthesis Example 12 | P-12 | M-12 | 15 | M-19 | 35 | M-24 | 50 | — | — | — | — | — | — | 14 | 32 | 54 | — | — | — | 8200 | 1.44 |
| Synthesis Example 13 | P-13 | M-13 | 20 | M-16 | 50 | M-27 | 30 | — | — | — | — | — | — | 18 | 46 | 36 | — | — | — | 10500 | 1.56 |
| Synthesis Example 14 | P-14 | M-14 | 30 | M-18 | 35 | M-23 | 35 | — | — | — | — | — | — | 28 | 32 | 40 | — | — | — | 9800 | 1.60 |
| Synthesis Example 15 | P-15 | M-1 | 20 | M-16 | 30 | M-22 | 35 | M-29 | 10 | — | — | — | — | 18 | 30 | 37 | 15 | — | — | 11200 | 1.41 |
| Synthesis Example 16 | P-16 | M-1 | 20 | M-16 | 30 | M-22 | 35 | M-29 | 10 | — | — | — | — | 19 | 31 | 37 | 15 | — | — | 13300 | 1.44 |
| Synthesis Example 17 | P-17 | M-1 | 20 | M-16 | 30 | M-22 | 35 | M-29 | 10 | — | — | — | — | 18 | 30 | 36 | 16 | — | — | 15400 | 1.50 |
| Synthesis Example 18 | P-18 | M-1 | 20 | M-16 | 35 | — | — | — | — | M-32 | 45 | — | — | 18 | 35 | — | — | 47 | — | 6800 | 1.59 |
| Synthesis Example 19 | P-19 | M-12 | 25 | M-16 | 20 | — | — | — | — | M-33 | 55 | — | — | 23 | 19 | — | — | 58 | — | 6900 | 1.68 |
| Synthesis Example 20 | P-20 | M-13 | 20 | M-17 | 20 | — | — | — | — | M-34 | 60 | — | — | 18 | 19 | — | — | 63 | — | 7000 | 1.43 |

TABLE 1-continued

| | Resin | Blending Amount of Compound Corresponding to Each Structural Unit (mol %) | | | | | | | | | | Content Rate of Each Structural Unit in Polymer (mol %) | | | | | | Physical Property Value | |
|---|---|---|---|---|---|---|---|---|---|---|---|---|---|---|---|---|---|---|---|
| | | Structural Unit (A) | | Structural Unit (B) | | Structural Unit (C) | | Structural Unit (D) | | Structural Unit (E) | | Comparative Structural Unit | | Structural Unit (A) | Structural Unit (B) | Structural Unit (C) | Structural Unit (D) | Structural Unit (E) | Comparative Structural Unit | | |
| | Type | Type | Blending Amount | Type | Blending Amount | Type | Blending Amount | Type | Blending Amount | Type | Blending Amount | Type | Blending Amount | | | | | | | Mw | Mw/Mn |
| Synthesis Example 21 | P-21 | M-1 | 10 | M-16 | 45 | — | — | — | — | M-35 | 45 | — | — | 9 | 42 | — | — | 49 | — | 6500 | 1.49 |
| Synthesis Example 22 | P-22 | M-2 | 30 | M-31 | 15 | — | — | — | — | M-36 | 55 | — | — | 28 | 14 | — | — | 58 | — | 6700 | 1.33 |
| Synthesis Example 23 | P-23 | M-1 | 40 | M-16 | 10 | — | — | M-30 | 15 | M-32 | 35 | — | — | 37 | 11 | — | 15 | 37 | — | 6700 | 1.56 |
| Synthesis Example 24 | P-24 | M-8 | 15 | M-31 | 25 | M-22 | 60 | — | — | — | — | — | — | 14 | 63 | 23 | — | — | — | 6700 | 1.55 |
| Synthesis Example 25 | P-25 | M-1 | 20 | M-16 | 35 | — | — | — | — | M-32 | 45 | — | — | 19 | 34 | — | — | 47 | — | 8300 | 1.66 |
| Synthesis Example 26 | P-26 | M-1 | 20 | M-16 | 35 | — | — | — | — | M-32 | 45 | — | — | 18 | 35 | — | — | 47 | — | 10100 | 1.77 |
| Synthesis Example 27 | P-27 | M-1 | 20 | M-16 | 35 | — | — | — | — | M-32 | 45 | — | — | 18 | 34 | — | — | 48 | — | 12400 | 1.81 |
| Synthesis Example 28 | P-28 | M-1 | 20 | M-16 | 35 | — | — | — | — | M-32 | 45 | — | — | 18 | 35 | — | — | 47 | — | 14600 | 1.82 |
| Synthesis Example 29 | P-29 | — | — | M-16 M-18 | 30 20 | M-22 | 35 | M-29 | 10 | — | — | — | — | — | 28 21 | 38 | 13 | — | — | 6500 | 1.41 |
| Synthesis Example 30 | P-30 | — | — | M-21 | 20 | M-23 | 55 | — | — | — | — | M-39 | 25 | 18 | 54 | 28 | — | — | — | 6400 | 1.38 |
| Synthesis Example 31 | P-31 | — | — | M-18 M-16 | 10 45 | — | — | — | — | M-35 | 45 | — | — | — | 9 43 | — | — | 48 | — | 6700 | 1.34 |
| Synthesis Example 32 | P-32 | — | — | M-31 | 15 | — | — | — | — | M-36 | 55 | M-39 | 30 | — | 15 | — | — | 58 | 27 | 6300 | 1.31 |

Synthesis of High Fluorine-Containing Resin

Synthesis Example 33: Synthesis of High Fluorine-Containing Resin (E-1)

Compounds (M-26) and (M-37) as monomers were dissolved in 2-butanone (200 parts by mass) at a molar ratio of 30/70. AIBN (5 mol % with respect to the total monomers) as an initiator was added thereto to prepare a monomer solution. 2-butanone (100 parts by mass) was placed in a reaction vessel, and the reaction vessel was purged with nitrogen gas for 30 minutes. The temperature in the reaction vessel was set at 80° C., and the monomer solution was added dropwise thereto under stirring for 3 hours. The polymerization reaction was performed for 6 hours with the start of the dropwise addition as the start time of the polymerization reaction. After the completion of the polymerization reaction, the polymerization solution was cooled with water to 30° C. or lower. The solvent was replaced with acetonitrile (400 parts by mass). Hexane (100 parts by mass) was then added and stirred, and an acetonitrile layer was collected. The collection was repeated three times in total. By replacing the solvent with propylene glycol monomethyl ether acetate, a solution of a high fluorine-containing resin (E-1) was obtained in a good yield.

Synthesis Example 34: Synthesis of High Fluorine-Containing Resin (E-2)

A high fluorine-containing resin (E-2) containing a predetermined amount of monomer shown in Table 2 was obtained in the same manner as in Synthesis Example 33. The Mw and Mw/Mn of each of the resulting high fluorine-containing resins, and the content rate of the structural unit derived from each of the monomers in each of the high fluorine-containing resins are shown together in Table 2. The compound (M-26), the compound (M-37), the compound (M-16), and the compound (M-38) respectively provide a structural unit (C), a structural unit (F), a structural unit (B), and a structural unit (D).

TABLE 2

| High Fluorine-Containing Resin | Blending Amount of Compound (mol %) | | | | Content Rate of Structural Unit Derived from Each Compound (mol %) | Physical Property Value | |
|---|---|---|---|---|---|---|---|
| | Blending Type | Blending Amount | Blending Type | Blending Amount | | Mw | Mw/Mn |
| Synthesis Example 33 | E-1 | M-26 | 30 | M-37 | 70 | M-26/M-37 = 31/69 | 5600 | 1.69 |
| Synthesis Example 34 | E-2 | M-16 | 50 | M-38 | 50 | M-16/M-38 = 46/54 | 6700 | 1.78 |

<Preparation of Radiation-Sensitive Resin Composition>

The following compounds were used as a radiation-sensitive acid generator, an acid diffusion inhibitor, and a solvent constituting a radiation-sensitive resin composition.

[Radiation-Sensitive Acid Generator]

C-1 to C-9: Compounds represented by the following formulae (C-1) to (C-9)

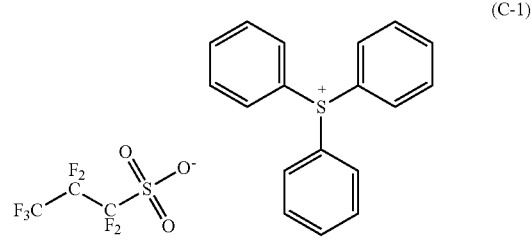
(C-1)

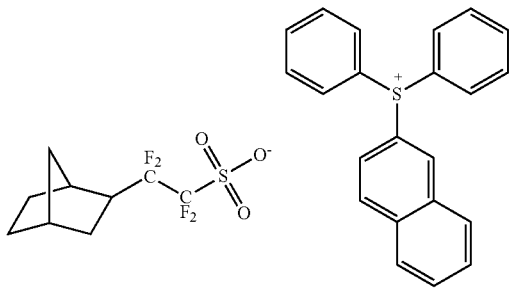
(C-2)

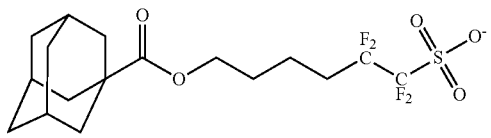
(C-3)

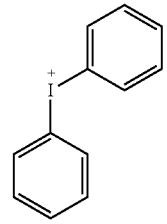

-continued

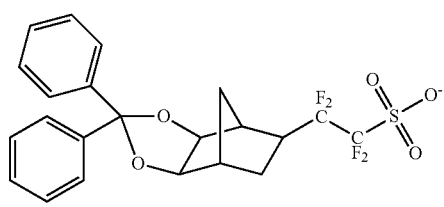
(C-4)

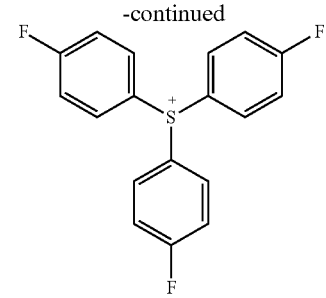
(C-5)
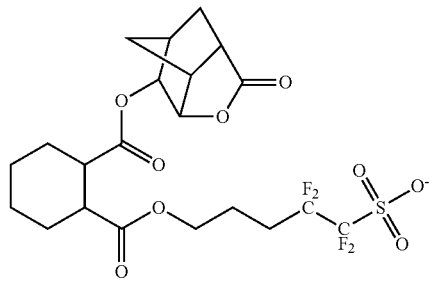
(C-6)
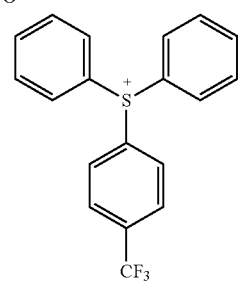
(C-7)
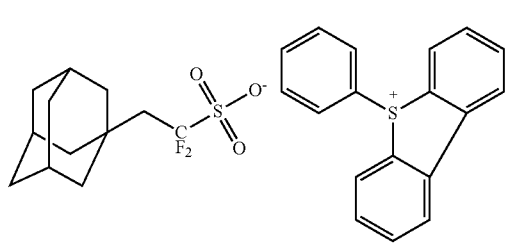
(C-8)
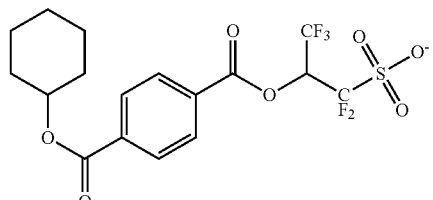
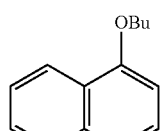
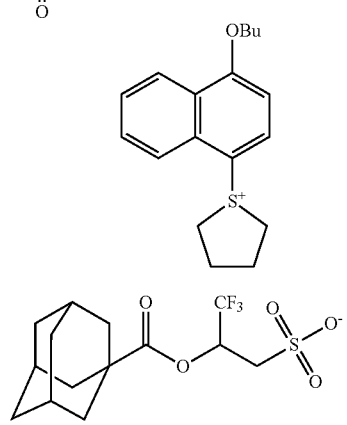
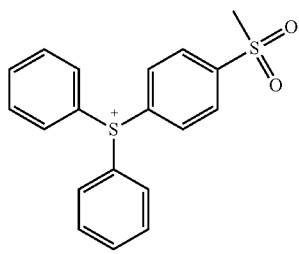
(C-9)
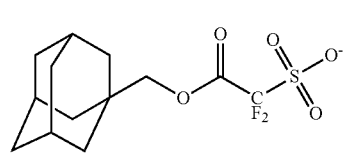
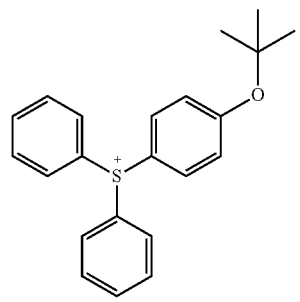
[Acid Diffusion Inhibitor]
D-1 to D-6: Compounds represented by the following formulae (D-1) to (D-6)
(D-1)
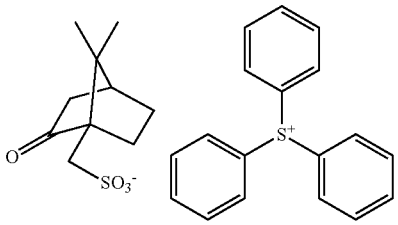
(D-2)

(D-3)

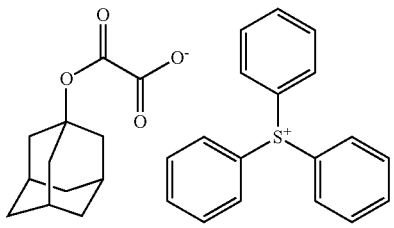

(D-6)

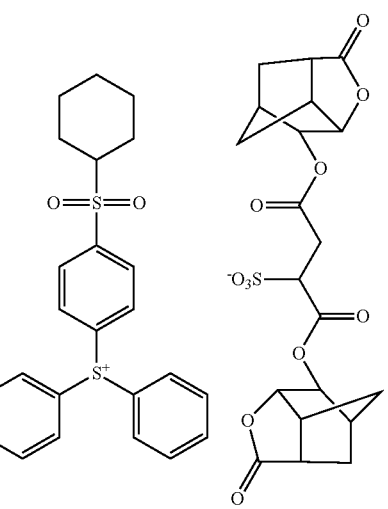

(D-4)

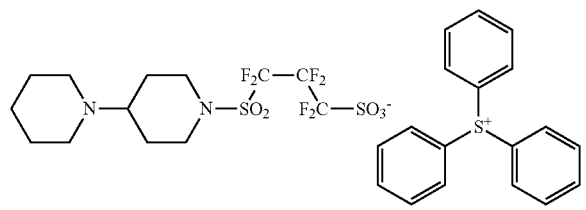

[Solvent]

F-1 to F-4: solvents represented by the following F-1 to F-4

F-1: propylene glycol monomethyl ether acetate

F-2: cyclohexanone

F-3: γ-butyrolactone

F-4: propylene glycol monomethyl ether

[Preparation of Radiation-Sensitive Resin Composition for ArF Exposure]

Example 1

(P-1) (100 parts by mass) as a resin, (C-4) (15.0 parts by mass) as a radiation-sensitive acid generator, (D-5) (2.5 parts by mass) as an acid diffusion inhibitor, (E-1) (7 parts by mass) as a high fluorine-containing resin, (F-1) (2,240 parts by mass) as a solvent, (F-2) (960 parts by mass), and (F-3) (30 parts by mass) were mixed, and the mixture was filtered through a 0.2 μm membrane filter to prepare a radiation-sensitive resin composition (J-1).

(D-5)

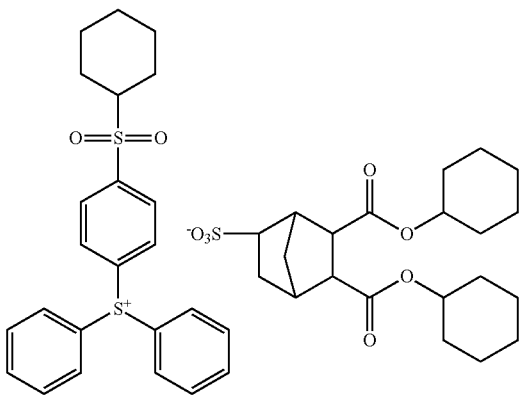

Example 2 to 17 and Comparative Example 1 and 2

Radiation-sensitive resin compositions (J-2) to (J-17) and (CJ-1) and (CJ-2) were prepared in the same manner as in Example 1 except that components of types and contents shown in the following Table 3 were used.

TABLE 3

| | Base Resin | | Radiation-Sensitive Acid Generator | | Acid Diffusion Controlling Agent | | High Fluorine-Containing Resin | | Solvent | |
|---|---|---|---|---|---|---|---|---|---|---|
| Radiation-Sensitive Resin Composition | Type | Content (Parts by Mass) | Type | Content (Parts by Mass) | Type | Content (Parts by Mass) | Type | Content (Parts by Mass) | Type | Content (Parts by Mass) |
| Example 1 | J-1 | P-1 | 100 | C-4 | 15.0 | D-5 | 2.5 | E-1 | 7 | F-1/F-2/F-3 | 2,240/960/30 |
| Example 2 | J-2 | P-2 | 100 | C-7 | 11.3 | D-1 | 3.0 | E-1 | 7 | F-1/F-2/F-3 | 2,240/960/30 |
| Example 3 | J-3 | P-3 | 100 | C-2 | 10.5 | D-6 | 3.3 | E-1 | 7 | F-1/F-2/F-3 | 2,240/960/30 |
| Example 4 | J-4 | P-4 | 100 | C-4 | 15.5 | D-1 | 2.5 | E-1 | 7 | F-1/F-2/F-3 | 2,240/960/30 |
| Example 5 | J-5 | P-5 | 100 | C-3 | 11.1 | D-2 | 2.6 | E-1 | 7 | F-1/F-2/F-3 | 2,240/960/30 |
| Example 6 | J-6 | P-6 | 100 | C-1 | 15.4 | D-2 | 4.0 | E-1 | 7 | F-1/F-2/F-3 | 2,240/960/30 |
| Example 7 | J-7 | P-7 | 100 | C-9 | 13.2 | D-5 | 3.1 | E-1 | 7 | F-1/F-2/F-3 | 2,240/960/30 |
| Example 8 | J-8 | P-8 | 100 | C-8 | 17.6 | D-1 | 1.5 | E-1 | 7 | F-1/F-2/F-3 | 2,240/960/30 |
| Example 9 | J-9 | P-9 | 100 | C-7 | 13.2 | D-3 | 3.2 | E-1 | 7 | F-1/F-2/F-3 | 2,240/960/30 |
| Example 10 | J-10 | P-10 | 100 | C-9 | 11.9 | D-3 | 2.5 | E-1 | 7 | F-1/F-2/F-3 | 2,240/960/30 |
| Example 11 | J-11 | P-11 | 100 | C-6 | 14.2 | D-3 | 2.0 | E-1 | 7 | F-1/F-2/F-3 | 2,240/960/30 |
| Example 12 | J-12 | P-12 | 100 | C-5 | 17.1 | D-4 | 3.1 | E-1 | 7 | F-1/F-2/F-3 | 2,240/960/30 |
| Example 13 | J-13 | P-13 | 100 | C-3 | 14.6 | D-4 | 1.9 | E-1 | 7 | F-1/F-2/F-3 | 2,240/960/30 |
| Example 14 | J-14 | P-14 | 100 | C-6 | 9.9 | D-1 | 2.0 | E-1 | 7 | F-1/F-2/F-3 | 2,240/960/30 |
| Example 15 | J-15 | P-15 | 100 | C-4 | 15.0 | D-S | 2.5 | E-1 | 7 | F-1/F-2/F-3 | 2,240/960/30 |
| Example 16 | J-16 | P-16 | 100 | C-4 | 15.0 | D-3 | 2.5 | E-1 | 7 | F-1/F-2/F-3 | 2,240/960/30 |
| Example 17 | J-17 | P-17 | 100 | C-4 | 15.0 | D-5 | 2.5 | E-1 | 7 | F-1/F-2/F-3 | 2,240/960/30 |
| Comparative Example 1 | CJ-1 | P-29 | 100 | C-4 | 15.0 | D-5 | 2.5 | E-1 | 7 | F-1/F-2/F-3 | 2,240/960/30 |
| Comparative Example 2 | CJ-2 | P-30 | 100 | C-7 | 11.3 | D-1 | 3.0 | E-1 | 7 | F-1/F-2/F-3 | 2,240/960/30 |

<Formation of Resist Pattern (1)> (ArF Exposure, Alkali Development)

Onto the surface of a 12-inch silicon wafer, an underlayer antireflection film forming composition ("ARC66" manufactured by Brewer Science Incorporated) was applied with use of a spin coater ("CLEAN TRACK ACT12" manufactured by Tokyo Electron Limited). The wafer was then heated at 205° C. for 60 seconds to form an underlayer antireflection film having a film thickness of 105 nm. Each radiation-sensitive resin composition for ArF exposure was applied onto the underlayer antireflection film with use of the spin coater, followed by performing PAB at 120° C. for 50 seconds. Thereafter, cooling was performed at 23° C. for 30 seconds to form a resist film having an average thickness of 90 nm. Next, the coating film was exposed through a mask pattern for forming a resist pattern having a space of 44 nm and a pitch of 102 nm with an ArF excimer laser immersion exposure apparatus ("TWINSCAN XT-1900i" manufactured by ASML) in optical conditions of NA=1.35 and Annular (σ=0.8/0.6). After exposing, PEB was performed at 90° C. for 60 seconds. Thereafter, paddle development was performed at 23° C. for 10 seconds using a 2.38 wt % aqueous TMAH solution, and spin drying was performed at 2,000 rpm for 15 seconds with shaking off, to form a resist pattern having a space of 45 nm.

<Evaluation>

The sensitivity, CDU, LWR, watermark defects, and residue defects of each of the radiation-sensitive resin compositions were evaluated by measuring each of the formed resist patterns according to the following method. A scanning electron microscope ("CG-5000" manufactured by Hitachi High-Tech Corporation) was used for measuring the length of the resist pattern.

[Sensitivity]

An exposure dose at which a 40-nm line-and-space pattern was formed in the aforementioned resist pattern formation using each of the radiation-sensitive resin compositions for ArF exposure was defined as an optimum exposure dose Eop, and this optimum exposure dose was adopted as sensitivity (mJ/cm$^2$). The sensitivity was evaluated to be "good" in a case of being mJ/cm$^2$ or less, and "poor" in a case of exceeding 25 mJ/cm$^2$.

[CDU Performance]

A resist pattern was formed by adjusting a mask size so as to form a pattern having a hole of 45 nm and a pitch of 110 nm by irradiation with the exposure dose Eop obtained above. The formed resist pattern was observed from above the pattern with use of the scanning electron microscope. The hole diameter was measured at 16 points within a square of 500 nm, and the measurement values were averaged to determine the average value. The average value was measured at five hundred of optional points. The 1 sigma value was calculated from the distribution of the measurement values, and defined as CDU performance (nm). The smaller the value of the CDU performance is, the smaller the variation in the hole diameter over long period is, which is better. The CDU performance can be evaluated to be "good" in a case of being 6.0 nm or less, and "poor" in a case of exceeding 6.0 nm.

[LWR Performance]

A resist pattern was formed by adjusting a mask size so as to form a pattern having a space of 45 nm and a pitch of 800 nm by irradiation with the exposure dose Eop obtained above. The formed resist pattern was observed from above the pattern with use of the scanning electron microscope. The variation in the line width was measured at a total of 500 points. The 3 sigma value was obtained from the distribution of the measurement values, and the 3 sigma value was defined as LWR performance (nm). The smaller the value of the LWR performance is, the smaller the wobble of the line is, which is better. The LWR performance can be evaluated to be "good" in a case of being 5.8 nm or less, and "poor" in a case of exceeding 5.8 nm.

[Watermark Defects, Residue Defects]

Watermark defects and residue defects in each resist pattern formed in the evaluation of the CDU and LWR performances were evaluated. The substrate on which the resist pattern had been formed was subjected to a defect test with use of a defect testing apparatus (KLA2810 manufactured by KLA-Tencor Corporation), and observed with use of a scanning electron microscope (RS6000 manufactured by Hitachi High-Tech Corporation), so as to evaluate the watermark defects and the residue defects according to the following evaluation criteria.

[Evaluation Criteria of Watermark Defects]

Good: the number of watermark defects was 0 per one wafer

Average: the number of watermark defects was 1 or more and less than 3 per one wafer Poor: the number of watermark defects was 3 or more per one wafer

[Evaluation Criteria of Residue Defects]

Good: the number of residue defects was less than 100 per one wafer

Poor: the number of residue defects was 100 or more per one wafer

[Evaluation of Receding Contact Angle of Water]

The receding contact angle (dRCA) of water on the surface of the film formed with use of each of the radiation-sensitive resin compositions for ArF exposure was evaluated. A 8-inch silicon wafer was spin-coated with the radiation-sensitive resin composition for ArF exposure, followed by performing PB at 90° C. for 60 seconds on a hot plate, to form an upper layer film having a film thickness of 30 nm. Thereafter, a receding contact angle was rapidly measured by the following procedure in an environment of room temperature of 23° C., a humidity of 45%, and an ordinary pressure with use of a contact angle meter (DSA-10 manufactured by KRUS). First, the wafer stage position of the contact angle meter was adjusted, and the wafer was set on the adjusted stage. Next, water was injected into a needle, and the position of the needle was finely adjusted to an initial position where a water droplet could be formed on the set wafer. Thereafter, water was discharged from the needle, and a water droplet of 25 μL was formed on the wafer. Then, the needle was temporarily drawn out from the water droplet, and the needle was pulled down at the initial position again and placed in the water droplet. Subsequently, the water droplet was sucked with the needle for 90 seconds at a speed of 10 μL/min and, at the same time, the contact angle was measured once per second for a total of 90 times. Among these, an average value of the contact angles for 20 seconds from the time point at which the measured value of the contact angle was stabilized was calculated, so as to determine the receding contact angle (unit: degree (°)).

The evaluation results of the sensitivity, CDU performance, LWR performance, defect-suppression performance, and receding contact angle of water will be shown below.

TABLE 4

| | Radiation-Sensitive Resin Composition | Sensitivity (mJ/cm$^2$) | CDU (nm) | LWR (nm) | Receding Contact Angle (°) | WM Defects | Residue Defects |
|---|---|---|---|---|---|---|---|
| Example 1 | J-1 | 24.3 | 5.80 | 5.39 | 80.2 | Good | Good |
| Example 2 | J-2 | 22.2 | 5.95 | 5.53 | 79.8 | Good | Good |
| Example 3 | J-3 | 23.1 | 5.46 | 5.08 | 80.7 | Good | Good |
| Example 4 | J-4 | 22.5 | 5.89 | 5.48 | 80.4 | Good | Good |
| Example 5 | J-5 | 23.7 | 5.61 | 5.22 | 79.1 | Good | Good |
| Example 6 | J-6 | 24.0 | 5.76 | 5.36 | 79.5 | Good | Good |
| Example 7 | J-7 | 24.3 | 5.55 | 5.16 | 80.9 | Good | Good |
| Example 8 | J-8 | 22.1 | 5.90 | 5.49 | 81.5 | Good | Good |
| Example 9 | J-9 | 23.2 | 5.70 | 5.30 | 81.0 | Good | Good |
| Example 10 | J-10 | 22.7 | 5.62 | 5.23 | 82.0 | Good | Good |
| Example 11 | J-11 | 23.7 | 5.61 | 5.22 | 80.1 | Good | Good |
| Example 12 | J-12 | 24.6 | 5.45 | 5.07 | 80.8 | Good | Good |
| Example 13 | J-13 | 24.0 | 5.45 | 5.07 | 81.5 | Good | Good |
| Example 14 | J-14 | 22.4 | 5.88 | 5.47 | 81.2 | Good | Good |
| Example 15 | J-15 | 23.0 | 5.55 | 5.16 | 79.8 | Good | Good |
| Example 16 | J-16 | 23.5 | 5.37 | 4.99 | 80.1 | Good | Good |
| Example 17 | J-17 | 23.0 | 5.53 | 5.14 | 80.5 | Good | Good |
| Comparative Example 1 | CJ-1 | 24.5 | 6.70 | 6.23 | 75.4 | Poor | Average |
| Comparative Example 2 | CJ-2 | 23.5 | 6.88 | 6.40 | 81.1 | Good | Poor |

As is apparent from the results in Table 4 above, the radiation-sensitive resin compositions in Examples had good CDU performance, LWR performance, and defect-suppression performance.

[Preparation of Radiation-Sensitive Resin Composition for Extreme Ultraviolet (EUV) Exposure]

Example 18

(P-18) (100 parts by mass) as a resin, (C-4) (25.8 parts by mass) as a radiation-sensitive acid generator, (D-2) (8.1 parts by mass) as an acid diffusion inhibitor, (E-2) (7 parts by mass) as a high fluorine-containing resin, and (F-1) (4,280 parts by mass) and (F-4) (1,830 parts by mass) as solvents were mixed, and the resulting mixture was filtered through a membrane filter having a pore size of 0.2 μm to prepare a radiation-sensitive resin composition (J-18).

Example 19 to 28 and Comparative Example 3 and 4

Radiation-sensitive resin compositions (J-19) to (J-28) and (CJ-3) and (CJ-4) were prepared in the same manner as in Example 18 except that components of types and contents shown in the following Table 5 were used.

TABLE 5

| | Radiation-Sensitive Resin Composition | Base Resin Type | Content (Parts by Mass) | Radiation-Sensitive Acid Generator Type | Content (Parts by Mass) | Acid Diffusion Inhibitor Type | Content (Parts by Mass) | High Fluorine-Containing Resin Type | Content (Parts by Mass) | Solvent Type | Content (Parts by Mass) |
|---|---|---|---|---|---|---|---|---|---|---|---|
| Example 18 | J-18 | P-18 | 100 | C-4 | 25.8 | D-2 | 8.1 | E-2 | 7 | F-1/F-4 | 4,280/1,830 |
| Example 19 | J-19 | P-19 | 100 | C-5 | 28.1 | D-2 | 8.1 | E-2 | 7 | F-1/F-4 | 4,280/1,830 |
| Example 20 | J-20 | P-20 | 100 | C-9 | 22.1 | D-2 | 8.1 | E-2 | 7 | F-1/F-4 | 4,280/1,830 |
| Example 21 | J-21 | P-21 | 100 | C-7 | 25.6 | D-3 | 9.2 | E-2 | 7 | F-1/F-4 | 4,280/1,830 |
| Example 22 | J-22 | P-22 | 100 | C-3 | 19.1 | D-2 | 8.1 | E-2 | 7 | F-1/F-4 | 4,280/1,830 |
| Example 23 | J-23 | P-23 | 100 | C-4 | 25.8 | D-3 | 9.2 | E-2 | 7 | F-1/F-4 | 4,280/1,830 |
| Example 24 | J-24 | P-24 | 100 | C-10 | 22.4 | D-3 | 9.2 | E-2 | 7 | F-1/F-4 | 4,280/1,830 |
| Example 25 | J-25 | P-25 | 100 | C-5 | 28.1 | D-2 | 8.1 | E-2 | 7 | F-1/F-4 | 4,280/1,830 |
| Example 26 | J-26 | P-26 | 100 | C-5 | 28.1 | D-2 | 8.1 | E-2 | 7 | F-1/F-4 | 4,280/1,830 |
| Example 27 | J-27 | P-27 | 100 | C-5 | 28.1 | D-2 | 8.1 | E-2 | 7 | F-1/F-4 | 4,280/1,830 |
| Example 28 | J-28 | P-28 | 100 | C-5 | 28.1 | D-2 | 8.1 | E-2 | 7 | F-1/F-4 | 4,280/1,830 |
| Comparative Example 3 | CJ-3 | P-31 | 100 | C-7 | 25.6 | D-3 | 9.2 | E-2 | 7 | F-1/F-4 | 4,280/1,830 |
| Comparative Example 4 | CJ-4 | P-32 | 100 | C-3 | 19.1 | D-2 | 8.1 | E-2 | 7 | F-1/F-4 | 4,280/1,830 |

<Formation of Resist Pattern Using Radiation-Sensitive Resin Composition for EUV Exposure>

Onto the surface of a 12-inch silicon wafer, an underlayer antireflection film forming composition ("ARC66" manufactured by Brewer Science Incorporated) was applied with use of a spin coater ("CLEAN TRACK ACT12" manufactured by Tokyo Electron Limited). The wafer was then heated at 205° C. for 60 seconds to form an underlayer antireflection film having an average film thickness of 105 nm. The radiation-sensitive resin composition for EUV exposure prepared above was applied onto the underlayer antireflection film with use of the spin coater, followed by performing PB at 130° C. for 60 seconds. Thereafter, cooling was performed at 23° C. for 30 seconds to form a resist film having an average thickness of 55 nm. Next, the resist film was exposed by an EUV exposure apparatus ("NXE3300", manufactured by ASML) with NA of 0.33 under a lighting condition of Conventional s=0.89 and with a mask of imecDEFECT32FFR02. After exposing, PEB was performed at 120° C. for 60 seconds. Thereafter, the resist film was developed with an alkali with use of a 2.38% by mass aqueous TMAH solution as an alkaline developer solution, followed by washing with water and further drying to form a positive resist pattern (32-nm line-and-space pattern).

<Evaluation>

The resist patterns formed using the radiation-sensitive resin compositions for EUV exposure were evaluated on sensitivity, CDU performance, and LWR performance according to the following methods. The results are shown in Table 6 below. A scanning electron microscope ("CG-5000" manufactured by Hitachi High-Tech Corporation) was used for measuring the length of the resist pattern.

[Sensitivity]

An exposure dose at which a 32-nm line-and-space pattern was formed in the aforementioned resist pattern formation using the radiation-sensitive resin composition for EUV exposure was defined as an optimum exposure dose Eop, and this optimum exposure dose was defined as sensitivity (mJ/cm$^2$). The sensitivity was evaluated to be "good" in a case of being 35 mJ/cm$^2$ or less, and "poor" in a case of exceeding 35 mJ/cm$^2$.

[CDU Performance]

A resist pattern was formed by adjusting a mask size so as to form a pattern having a hole of 35 nm and a pitch of 90 nm by irradiation with the exposure dose Eop obtained above. The formed resist pattern was observed from above the pattern with use of the scanning electron microscope. The hole diameter was measured at 16 points within a square of 500 nm, and the measurement values were averaged to determine the average value. The average value was measured at five hundred of optional points. The 1 sigma value was calculated from the distribution of the measurement values, and defined as CDU performance (nm). The smaller the value of the CDU performance is, the smaller the variation in the hole diameter over long period is, which is better. The CDU performance was evaluated to be "good" in a case of being 2.0 nm or less, and "poor" in a case of exceeding 2.0 nm.

[LWR Performance]

A resist pattern was formed by adjusting a mask size so as to form a 32-nm line-and-space pattern by irradiation with the optimum exposure dose Eop obtained in the evaluation of the sensitivity. The formed resist pattern was observed from above the pattern with use of the scanning electron microscope. The variation in the line width was measured at a total of 500 points. The 3 sigma value was obtained from the distribution of the measurement values, and defined as LWR performance (nm). The smaller the value of the LWR is, the smaller the wobble of the line is, which is better. The LWR performance was evaluated to be "good" in a case of being 2.5 nm or less, and "poor" in a case of exceeding 2.5 nm.

The evaluation results of the sensitivity, LWR performance, and CDU performance are shown in Table 6 below.

TABLE 6

| | Radiation-Sensitive Resin Composition | Sensitivity (mJ/cm$^2$) | CDU (nm) | LWR (nm) |
|---|---|---|---|---|
| Example 18 | J-18 | 33.6 | 1.81 | 2.26 |
| Example 19 | J-19 | 33.2 | 1.89 | 2.36 |
| Example 20 | J-20 | 33.8 | 1.85 | 2.31 |
| Example 21 | J-21 | 34.5 | 1.79 | 2.23 |

TABLE 6-continued

| | Radiation-Sensitive Resin Composition | Sensitivity (mJ/cm$^2$) | CDU (nm) | LWR (nm) |
|---|---|---|---|---|
| Example 22 | J-22 | 32.0 | 1.91 | 2.38 |
| Example 23 | J-23 | 31.4 | 1.94 | 2.42 |
| Example 24 | J-24 | 34.0 | 1.83 | 2.28 |
| Example 25 | J-25 | 33.5 | 1.80 | 2.24 |
| Example 26 | J-26 | 33.0 | 1.73 | 2.22 |
| Example 27 | J-27 | 34.0 | 1.78 | 2.16 |
| Example 28 | J-28 | 32.5 | 1.80 | 2.24 |
| Comparative Example 3 | CJ-3 | 37.4 | 2.33 | 3.11 |
| Comparative Example 4 | CJ-4 | 36.8 | 2.44 | 3.21 |

As is apparent from the results in Table 6 above, the radiation-sensitive resin compositions in Examples had good sensitivity, CDU performance, and LWR performance.

According to the radiation-sensitive resin composition and the method for forming a resist pattern of the embodiments of the present invention, a resist pattern having small CDU and LWR and few defects such as watermark can be formed. Therefore, these can be suitably used for a machining process and the like of a semiconductor device in which micronization is expected to progress more and more in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising:
   a resin having a partial structure represented by formula (1);
   a radiation-sensitive acid generator; and
   a solvent;

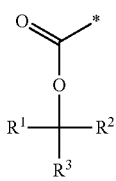
(1)

wherein, in the formula (1), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded;

$R^3$ represents a monovalent alicyclic hydrocarbon group having 4 to 20 carbon atoms and comprising an alicyclic ring, wherein the alicyclic ring comprises —$CF_2$— group, and the carbon atom of the —$CF_2$— group is a ring atom of the alicyclic ring;

provided that in $R^1$ and $R^2$, no fluorine atom is bonded to carbon atoms located at α-, β- and γ-positions of the carbon atom to which $R^1$ and $R^2$ are bonded;

in $R^3$, no fluorine atom is bonded to carbon atoms located at α- and β-positions of the carbon atom to which $R^3$ is bonded; and

* represents a bond.

2. The radiation-sensitive resin composition according to claim 1, wherein the partial structure represented by the formula (1) is a partial structure represented by formula (1-1-1), a partial structure represented by formula (1-1-2), a partial structure represented by formula (1-1-3), or a partial structure represented by formula (1-1-4):

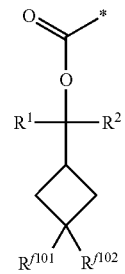
(1-1-1)

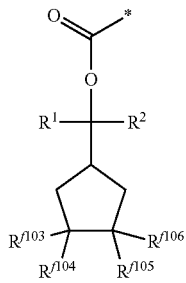
(1-1-2)

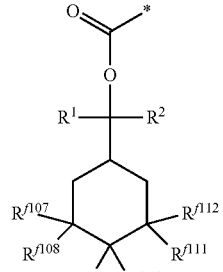
(1-1-3)

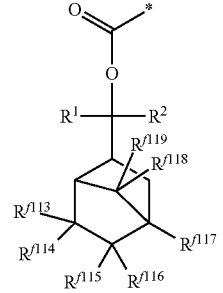
(1-1-4)

wherein, in the formulae (1-1-1), (1-1-2), (1-1-3), and (1-1-4), $R^1$ and $R^2$ have the same meanings as those in the formula (1);

$R^{f101}$ and $R^{f102}$ are each a fluorine atom, and $R^{f103}$ to $R^{f119}$ each independently represent a fluorine atom, a fluorinated alkyl group having 1 to 3 carbon atoms, a hydrogen atom, or an alkyl group having 1 to 3 carbon atoms;

provided that at least one of $R^{f103}$—C—$R^{f104}$ and $R^{f105}$—C—$R^{f106}$, at least one of $R^{f107}$—C—$R^{f108}$, $R^{f109}$—C—

$R^{f110}$ and $R^{f111}$—C—$R^{f112}$, and at least one of $R^{f113}$—C—$R^{f114}$, $R^{f115}$—C—$R^{f116}$ and $R^{f118}$—C—$R^{f119}$ are —$CF_2$— group; and

* represents a bond.

3. The radiation-sensitive resin composition according to claim 1, wherein the partial structure represented by the formula (1) is a partial structure represented by formula (1-2-1), a partial structure represented by formula (1-2-2), or a partial structure represented by formula (1-2-3):

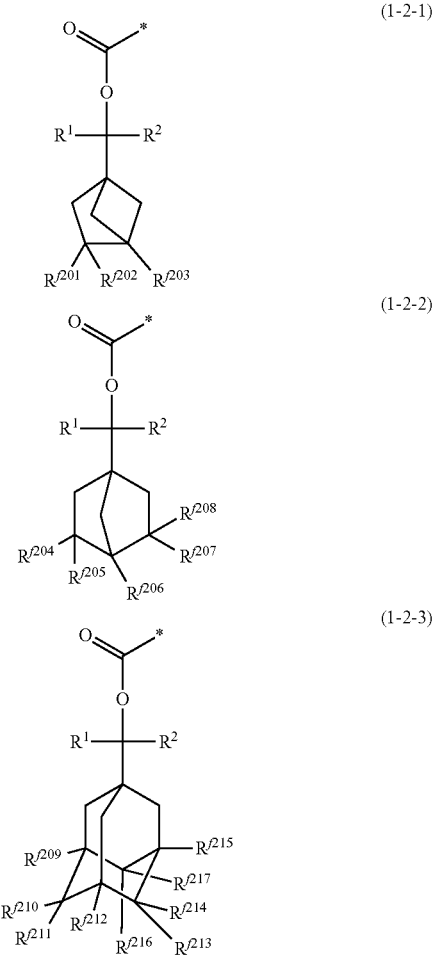

wherein, in the formulae (1-2-1), (1-2-2), and (1-2-3),
$R^1$ and $R^2$ have the same meanings as those in the formula (1);
$R^{f201}$ and $R^{f202}$ are each a fluorine atom, and $R^{f203}$ to $R^{f217}$ each independently represent a fluorine atom, a fluorinated alkyl group having 1 to 3 carbon atoms, a hydrogen atom, or an alkyl group having 1 to 3 carbon atoms;
provided at least one of $R^{f204}$—C—$R^{f205}$ and $R^{f207}$—C—$R^{f208}$, and at least one of $R^{f210}$—C—$R^{f211}$, $R^{f213}$—C—$R^{f214}$ and $R^{f216}$—C—$R^{f217}$ are —$CF_2$— group; and
* represents a bond.

4. The radiation-sensitive resin composition according to claim 1, wherein a content of a structural unit having the partial structure represented by the formula (1) in the resin is 5 mol % or more and 40 mol % or less.

5. A method for forming a resist pattern, comprising:
forming a resist film from the radiation-sensitive resin composition according to claim 1;
exposing the resist film; and
developing the exposed resist film.

6. The method for forming a resist pattern according to claim 5, wherein the exposure is performed with use of ArF excimer laser light or extreme ultraviolet light.

7. The method for forming a resist pattern according to claim 5, wherein the partial structure represented by the formula (1) is a partial structure represented by formula (1-1-1), a partial structure represented by formula (1-1-2), a partial structure represented by formula (1-1-3), or a partial structure represented by formula (1-1-4):

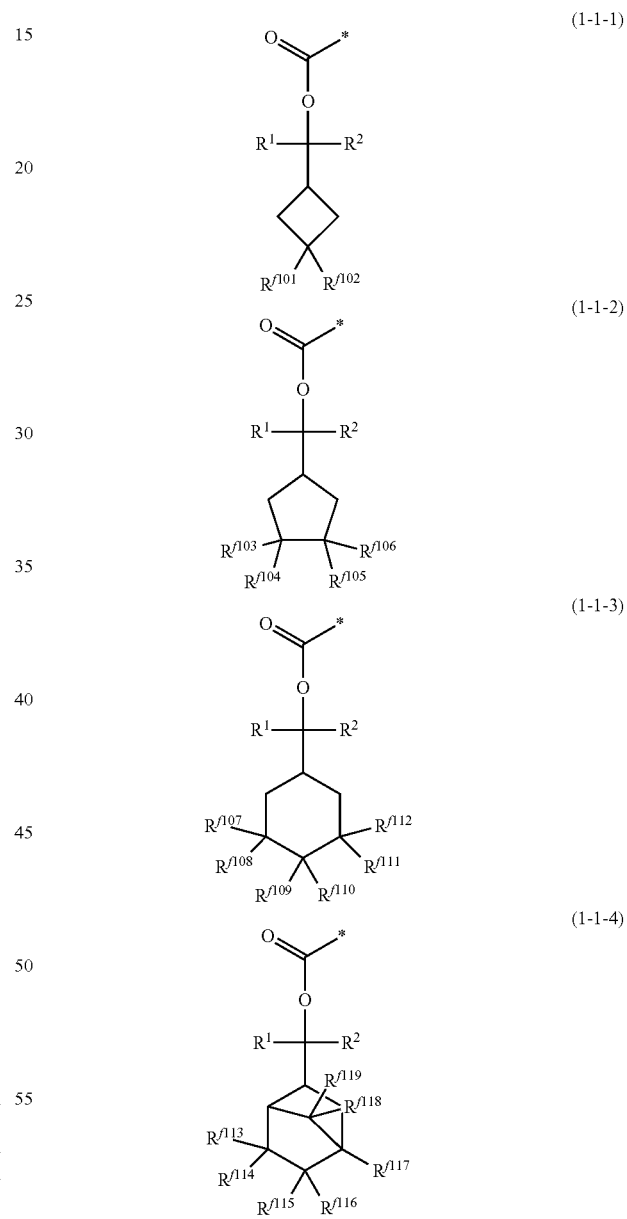

wherein, in the formulae (1-1-1), (1-1-2), (1-1-3), and (1-1-4),
$R^1$ and $R^2$ have the same meanings as those in the formula (1);
$R^{f101}$ and $R^{f102}$ are each a fluorine atom, and $R^{f103}$ to $R^{f119}$ each independently represent a fluorine atom, a fluorinated alkyl group having 1 to 3 carbon atoms, a hydrogen atom, or an alkyl group having 1 to 3 carbon atoms;

provided that at least one of $R'^{103}$—C—$R'^{104}$ and $R'^{105}$—C—$R'^{106}$, at least one of $R'^{107}$—C—$R'^{108}$, $R'^{109}$—C—$R'^{110}$ and $R'^{111}$—C—$R'^{112}$, and at least one of $R'^{113}$—C—$R'^{114}$, $R'^{115}$—C—$R'^{116}$ and $R'^{118}$—C—$R'^{119}$ are $CF_2$; and \* represents a bond.

8. The method for forming a resist pattern according to claim 5, wherein the partial structure represented by the formula (1) is a partial structure represented by formula (1-2-1), a partial structure represented by formula (1-2-2), or a partial structure represented by formula (1-2-3):

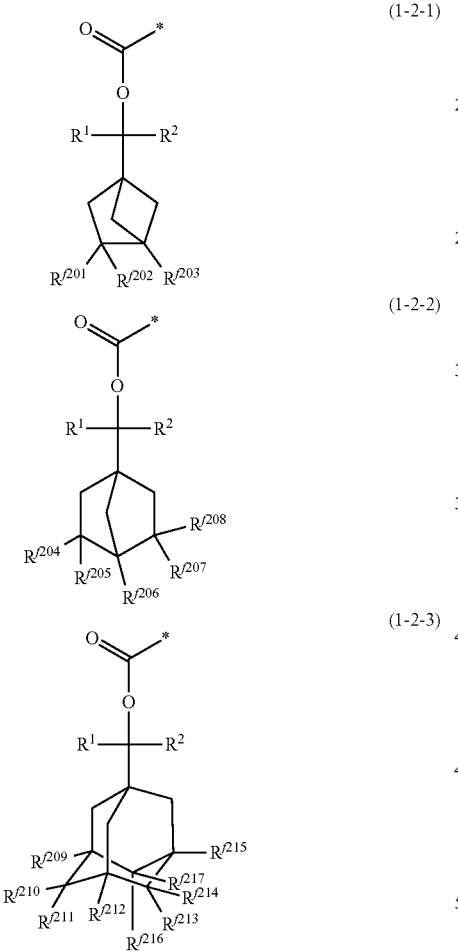

wherein, in the formulae (1-2-1), (1-2-2), and (1-2-3), $R^1$ and $R^2$ have the same meanings as those in the formula (1);

$R'^{201}$ and $R'^{202}$ are each a fluorine atom, and $R'^{203}$ to $R'^{217}$ each independently represent a fluorine atom, a fluorinated alkyl group having 1 to 3 carbon atoms, a hydrogen atom, or an alkyl group having 1 to 3 carbon atoms;

provided at least one of $R'^{204}$—C—$R'^{205}$ and $R'^{207}$—C—$R'^{208}$, and at least one of $R'^{210}$—C—$R'^{211}$, $R'^{213}$—C—$R'^{214}$ and $R'^{216}$—C—$R'^{217}$ are $CF_2$; and \* represents a bond.

9. The method for forming a resist pattern according to claim 5, wherein a content of a structural unit having the partial structure represented by the formula (1) in the resin is 5 mol % or more and 40 mol % or less.

10. The method for forming a resist pattern according to claim 5, wherein the resin comprises a first structural unit, and the partial structure represented by the formula (1) is introduced as a side chain structure of the first structural unit.

11. The method for forming a resist pattern according to claim 10, wherein the resin further comprises a second structural unit which comprises an acid-dissociable group.

12. The method for forming a resist pattern according to claim 10, wherein the resin further comprises a third structural unit which comprises a group comprising at least one structure selected from the group consisting of a lactone structure, a cyclic carbonate structure, and a sultone structure.

13. The radiation-sensitive resin composition according to claim 1, wherein the resin comprises a first structural unit, and the partial structure represented by the formula (1) is introduced as a side chain structure of the first structural unit.

14. The radiation-sensitive resin composition according to claim 13, wherein the resin further comprises a second structural unit which comprises an acid-dissociable group.

15. The radiation-sensitive resin composition according to claim 14, wherein a content of the second structural unit is 10 to 70 mol % relative to total structural units in the resin.

16. The radiation-sensitive resin composition according to claim 13, wherein the resin further comprises a third structural unit which comprises a group comprising at least one structure selected from the group consisting of a lactone structure, a cyclic carbonate structure, and a sultone structure.

17. The radiation-sensitive resin composition according to claim 16, wherein a content of the third structural unit is 20 to 70 mol % relative to total structural units in the resin.

18. A compound represented by formula (I):

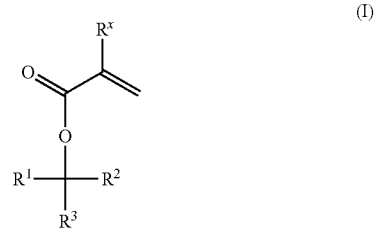

wherein, in the formula (I), $R^x$ is a hydrogen atom, a fluorine atom, a methyl group, or a trifluoromethyl group;

$R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded;

$R^3$ represents a monovalent alicyclic hydrocarbon group having 4 to 20 carbon atoms and comprising an alicyclic ring, wherein the alicyclic ring comprises —$CF_2$— group, and the carbon atom of the —$CF_2$— group is a ring atom of the alicyclic ring;

provided that in $R^1$ and $R^2$, no fluorine atom is bonded to carbon atoms located at α-, β- and γ-positions of the carbon atom to which $R^1$ and $R^2$ are bonded; and in $R^3$, no fluorine atom is bonded to carbon atoms located at α- and β-positions of the carbon atom to which $R^3$ is bonded.

19. A compound represented by formula (i):

(i)

wherein, in the formula (i), $R^1$ and $R^2$ each independently represent a substituted or unsubstituted chain aliphatic hydrocarbon group having 1 to 6 carbon atoms or a substituted or unsubstituted alicyclic hydrocarbon group having 3 to 6 carbon atoms, or $R^1$ and $R^2$ are bonded to each other to form a part of a 3- to 6-membered cyclic structure together with the carbon atom to which $R^1$ and $R^2$ are bonded;

$R^3$ represents a monovalent alicyclic hydrocarbon group having 4 to 20 carbon atoms and comprising an alicyclic ring, wherein the alicyclic ring comprises —$CF_2$— group, and the carbon atom of the —$CF_2$— group is a ring atom of the alicyclic ring;

provided that in $R^1$ and $R^2$, no fluorine atom is bonded to carbon atoms located at α-, β- and γ-positions of the carbon atom to which $R^1$ and $R^2$ are bonded; and in $R^3$, no fluorine atom is bonded to carbon atoms located at α- and β-positions of the carbon atom to which $R^3$ is bonded.

\* \* \* \* \*